US011253237B2

(12) United States Patent
Daly et al.

(10) Patent No.: US 11,253,237 B2
(45) Date of Patent: Feb. 22, 2022

(54) MRI COMPATIBLE INTRABODY FLUID TRANSFER SYSTEMS AND RELATED DEVICES AND METHODS

(71) Applicant: ClearPoint Neuro, Inc., Irvine, CA (US)

(72) Inventors: Maxwell Jerad Daly, Redlands, CA (US); Rajesh Pandey, Irvine, CA (US)

(73) Assignee: ClearPoint Neuro, Inc., Irvine, CA (US)

( * ) Notice: Subject to any disclaimer, the term of this patent is extended or adjusted under 35 U.S.C. 154(b) by 0 days.

(21) Appl. No.: 16/217,273

(22) Filed: Dec. 12, 2018

(65) Prior Publication Data

US 2019/0343496 A1     Nov. 14, 2019

Related U.S. Application Data

(60) Provisional application No. 62/668,920, filed on May 9, 2018.

(51) Int. Cl.
    *A61B 10/02*           (2006.01)
    *A61B 17/34*           (2006.01)
    (Continued)

(52) U.S. Cl.
    CPC ...... *A61B 10/0275* (2013.01); *A61B 10/0283* (2013.01); *A61B 17/3403* (2013.01);
    (Continued)

(58) Field of Classification Search
    CPC ....... G01R 33/285; A61B 34/20; A61B 90/37; A61B 10/0275; A61B 10/0283; A61B 17/3403; A61B 17/3421; A61B 2034/107; A61B 2090/364; A61B 2090/374; A61B 5/055; A61B 2017/00911; A61B 2090/062; A61B 2090/103; A61B 90/11;
    (Continued)

(56) References Cited

U.S. PATENT DOCUMENTS

| | | |
|---|---|---|
| 3,352,306 A | 11/1967 | Hrisch |
| 3,540,447 A | 11/1970 | Howe |

(Continued)

FOREIGN PATENT DOCUMENTS

| | | |
|---|---|---|
| CA | 2655515 | 8/2010 |
| EP | 1029509 | 8/2000 |

(Continued)

OTHER PUBLICATIONS

U.S. Appl. No. 16/217,222, filed Dec. 12, 2018, Piferi.

(Continued)

*Primary Examiner* — Amber R Stiles
(74) *Attorney, Agent, or Firm* — Myers Bigel, P.A.

(57) ABSTRACT

Systems and methods for transferring fluid to or from a subject use a set of MRI compatible components that can aspirate intrabody structure and/or fluids. The components include a device guide, a semi-rigid guide sheath configured to slidably extend through the device guide, a stylet releasable coupled to the guide sheath and extending a fixed distance out of a distal end thereof, and a cannula coupled to flexible tubing that is releasably interchangeably held in the guide sheath in lieu of the stylet.

25 Claims, 11 Drawing Sheets

(51) Int. Cl.
*A61B 34/20* (2016.01)
*G01R 33/28* (2006.01)
*A61B 90/00* (2016.01)
*A61M 25/01* (2006.01)
*A61B 5/055* (2006.01)
*A61B 34/10* (2016.01)

(52) U.S. Cl.
CPC .......... *A61B 17/3421* (2013.01); *A61B 34/20* (2016.02); *A61B 90/37* (2016.02); *G01R 33/285* (2013.01); *A61B 5/055* (2013.01); *A61B 2034/107* (2016.02); *A61B 2090/364* (2016.02); *A61B 2090/374* (2016.02); *A61M 25/01* (2013.01)

(58) Field of Classification Search
CPC .............. A61B 17/3417; A61M 25/01; A61M 2025/0004; A61M 2025/0006; A61M 2005/3201; A61M 5/3295; A61M 5/3297
See application file for complete search history.

(56) References Cited

U.S. PATENT DOCUMENTS

| | | |
|---|---|---|
| 3,824,157 A | 7/1974 | Macur |
| 3,856,009 A | 12/1974 | Winnie |
| 4,149,535 A | 4/1979 | Volder |
| 4,239,042 A | 12/1980 | Asai |
| 4,265,928 A | 5/1981 | Braun |
| 4,327,722 A | 5/1982 | Groshong et al. |
| 4,449,532 A | 5/1984 | Storz |
| 4,531,943 A | 7/1985 | Van Tassel et al. |
| 4,543,091 A | 9/1985 | Froning et al. |
| 4,543,092 A | 9/1985 | Mehler et al. |
| 4,597,421 A | 7/1986 | Wells |
| 4,623,789 A | 11/1986 | Ikeda et al. |
| 4,629,450 A | 12/1986 | Suzuki et al. |
| 4,705,511 A | 11/1987 | Kocak |
| 4,738,658 A | 4/1988 | Magro et al. |
| 4,739,768 A | 4/1988 | Engelson |
| 4,781,691 A | 11/1988 | Gross |
| 4,820,349 A | 4/1989 | Saab |
| 4,846,799 A | 7/1989 | Tanaka et al. |
| 4,897,077 A | 1/1990 | Cicciu et al. |
| 4,955,863 A | 9/1990 | Walker et al. |
| 4,978,334 A | 12/1990 | Toye et al. |
| 4,995,866 A | 2/1991 | Amplatz et al. |
| 5,069,673 A | 12/1991 | Shwab |
| 5,380,292 A | 1/1995 | Wilson |
| 5,562,626 A | 10/1996 | Sanpietro |
| 5,699,801 A | 12/1997 | Atalar et al. |
| 5,720,720 A | 2/1998 | Laske et al. |
| 5,722,985 A | 3/1998 | Pettus |
| 5,792,144 A | 8/1998 | Fischell et al. |
| 5,833,662 A | 11/1998 | Stevens |
| 5,851,203 A | 12/1998 | van Muiden |
| 5,857,999 A | 1/1999 | Quick et al. |
| 5,871,470 A | 2/1999 | McWha |
| 5,902,282 A | 5/1999 | Balbierz |
| 5,919,171 A | 7/1999 | Kira et al. |
| 5,928,145 A | 7/1999 | Ocali et al. |
| 5,935,122 A | 8/1999 | Fourkas et al. |
| 6,020,196 A | 2/2000 | Hu et al. |
| 6,026,316 A | 2/2000 | Kucharczyk et al. |
| 6,030,369 A | 2/2000 | Engelson et al. |
| 6,042,579 A | 3/2000 | Elsberry et al. |
| 6,050,992 A | 4/2000 | Nichols |
| 6,093,180 A | 7/2000 | Elsberry |
| 6,167,311 A | 12/2000 | Rezai |
| 6,186,986 B1 | 2/2001 | Berg et al. |
| 6,231,591 B1 | 5/2001 | Desai |
| 6,263,229 B1 | 7/2001 | Atalar et al. |
| 6,284,971 B1 | 9/2001 | Atalar et al. |
| RE37,410 E | 10/2001 | Brem et al. |
| 6,309,634 B1 | 10/2001 | Bankiewicz et al. |
| 6,336,915 B1 | 1/2002 | Scarfone et al. |
| 6,356,786 B1 | 3/2002 | Rezai et al. |
| 6,405,079 B1 | 6/2002 | Ansarinia |
| 6,438,423 B1 | 8/2002 | Rezai et al. |
| 6,461,296 B1 | 10/2002 | Desai |
| 6,524,299 B1 | 2/2003 | Tran et al. |
| 6,526,318 B1 | 2/2003 | Ansarinia |
| 6,533,751 B2 | 3/2003 | Cragg et al. |
| 6,539,263 B1 | 3/2003 | Schiff et al. |
| 6,551,290 B1 | 4/2003 | Elsberry et al. |
| 6,585,694 B1 | 7/2003 | Smith et al. |
| 6,606,513 B2 | 8/2003 | Lardo et al. |
| 6,609,030 B1 | 8/2003 | Rezai et al. |
| 6,628,980 B2 | 9/2003 | Atalar et al. |
| 6,641,555 B1 | 11/2003 | Botich et al. |
| 6,641,564 B1 | 11/2003 | Kraus |
| 6,675,033 B1 | 1/2004 | Lardo et al. |
| 6,689,142 B1 | 2/2004 | Tremaglio, Jr. et al. |
| 6,701,176 B1 | 3/2004 | Halperin et al. |
| 6,708,064 B2 | 3/2004 | Rezai |
| 6,904,307 B2 | 6/2005 | Karmarkar et al. |
| 7,037,295 B2 | 5/2006 | Tiernan et al. |
| 7,182,944 B2 | 2/2007 | Bankiewicz |
| 7,329,262 B2 | 2/2008 | Gill |
| 7,341,577 B2 | 3/2008 | Gill |
| 7,351,239 B2 | 4/2008 | Gill |
| 7,371,225 B2 | 5/2008 | Oldfield et al. |
| 7,780,692 B2 | 8/2010 | Nance et al. |
| 7,815,623 B2 | 10/2010 | Bankiewicz et al. |
| 7,892,203 B2 | 2/2011 | Lenker et al. |
| 7,951,110 B2 | 5/2011 | Bishop et al. |
| 8,128,600 B2 | 3/2012 | Gill |
| 8,175,677 B2 | 5/2012 | Sayler et al. |
| 8,195,272 B2 | 6/2012 | Piferi et al. |
| 8,315,689 B2 | 11/2012 | Jenkins et al. |
| 8,340,743 B2 | 12/2012 | Jenkins et al. |
| 8,348,892 B2 | 1/2013 | Lenker et al. |
| 8,374,677 B2 | 2/2013 | Piferi et al. |
| 8,597,277 B2 | 12/2013 | Lenker et al. |
| 8,827,987 B2 | 9/2014 | Fielder et al. |
| 8,900,214 B2 | 12/2014 | Nance et al. |
| 9,044,577 B2 | 6/2015 | Bishop et al. |
| 9,050,419 B2 | 6/2015 | Farnan |
| 9,452,241 B2 | 9/2016 | Gill et al. |
| 9,498,575 B2 | 11/2016 | Flores |
| 9,572,928 B2 | 2/2017 | Shifflette et al. |
| 9,610,048 B2 | 4/2017 | Vij et al. |
| 9,891,296 B2 | 2/2018 | Piferi |
| 10,105,485 B2 | 10/2018 | Piferi et al. |
| 10,576,247 B2 | 3/2020 | Flores et al. |
| 2002/0087152 A1 | 7/2002 | Mikus et al. |
| 2002/0091372 A1 | 7/2002 | Cragg et al. |
| 2002/0095081 A1 | 7/2002 | Vilsmeier |
| 2002/0114780 A1 | 8/2002 | Bankiewicz et al. |
| 2002/0141980 A1 | 10/2002 | Bankiewicz et al. |
| 2002/0183763 A1 | 12/2002 | Callol et al. |
| 2003/0028095 A1 | 2/2003 | Tulley et al. |
| 2003/0050557 A1 | 3/2003 | Susil et al. |
| 2003/0073934 A1 | 4/2003 | Putz |
| 2003/0130575 A1 | 7/2003 | Desai |
| 2003/0216714 A1 | 11/2003 | Gill |
| 2004/0044329 A1 | 3/2004 | Trudell |
| 2004/0046557 A1 | 3/2004 | Karmarkar et al. |
| 2004/0064098 A1 | 4/2004 | Cuschieri et al. |
| 2004/0068190 A1* | 4/2004 | Cespedes ................ A61B 8/12 600/466 |
| 2004/0092879 A1 | 5/2004 | Kraus et al. |
| 2004/0199129 A1 | 10/2004 | DiMatteo |
| 2004/0209810 A1 | 10/2004 | Gill et al. |
| 2004/0215162 A1 | 10/2004 | Putz |
| 2004/0249261 A1 | 12/2004 | Torchia et al. |
| 2005/0004504 A1 | 1/2005 | Frye et al. |
| 2005/0112065 A1 | 5/2005 | Drummond et al. |
| 2005/0148865 A1 | 7/2005 | Weber |
| 2005/0154297 A1 | 7/2005 | Gill |
| 2005/0256503 A1 | 11/2005 | Hall |
| 2006/0052750 A1 | 3/2006 | Lenker et al. |
| 2006/0073101 A1 | 4/2006 | Oldfield et al. |
| 2006/0129126 A1 | 6/2006 | Kaplitt et al. |

(56) References Cited

U.S. PATENT DOCUMENTS

| | | |
|---|---|---|
| 2006/0135945 A1 | 6/2006 | Bankiewicz et al. |
| 2006/0217664 A1 | 9/2006 | Hattler et al. |
| 2007/0088295 A1 | 4/2007 | Bankiewicz |
| 2007/0110798 A1 | 5/2007 | Drummond et al. |
| 2007/0167736 A1 | 7/2007 | Dietz et al. |
| 2007/0179455 A1 | 8/2007 | Geliebter et al. |
| 2007/0250021 A1 | 10/2007 | Brimhall et al. |
| 2007/0254842 A1 | 11/2007 | Bankiewicz |
| 2008/0103456 A1 | 5/2008 | Johnson et al. |
| 2008/0119821 A1 | 5/2008 | Agnihotri et al. |
| 2008/0215008 A1 | 9/2008 | Nance et al. |
| 2008/0228168 A1 | 9/2008 | Mittermeyer et al. |
| 2008/0319377 A1 | 12/2008 | Keenan |
| 2009/0088695 A1 | 4/2009 | Kapur et al. |
| 2009/0088730 A1 | 4/2009 | Hoofnagle et al. |
| 2009/0112084 A1 | 4/2009 | Piferi et al. |
| 2009/0118610 A1 | 5/2009 | Karmarkar et al. |
| 2009/0143764 A1 | 6/2009 | Nelson |
| 2009/0171184 A1 | 7/2009 | Jenkins et al. |
| 2009/0198218 A1 | 8/2009 | Gill et al. |
| 2009/0209937 A1 | 8/2009 | Rogawski et al. |
| 2009/0281453 A1 | 11/2009 | Tsonton et al. |
| 2010/0130958 A1 | 5/2010 | Kang et al. |
| 2010/0198052 A1 | 8/2010 | Jenkins et al. |
| 2010/0217228 A1* | 8/2010 | Grahn .............. A61M 25/0068 604/500 |
| 2010/0217236 A1 | 8/2010 | Gill et al. |
| 2010/0228122 A1 | 9/2010 | Keenan et al. |
| 2010/0317961 A1 | 12/2010 | Jenkins et al. |
| 2010/0318061 A1 | 12/2010 | Derrick et al. |
| 2010/0318064 A1 | 12/2010 | Derrick et al. |
| 2011/0282319 A1 | 11/2011 | Gill |
| 2012/0123391 A1 | 5/2012 | Gill et al. |
| 2012/0310182 A1 | 12/2012 | Fielder et al. |
| 2013/0006095 A1 | 1/2013 | Jenkins et al. |
| 2013/0030408 A1 | 1/2013 | Piferi et al. |
| 2013/0150712 A1* | 6/2013 | Field ..................... A61M 25/09 600/424 |
| 2013/0226094 A1* | 8/2013 | Ahmed .............. A61B 17/3421 604/164.04 |
| 2014/0257168 A1 | 9/2014 | Gill |
| 2014/0343500 A1 | 11/2014 | Fielder et al. |
| 2015/0080708 A1* | 3/2015 | Piferi ................. A61B 10/0233 600/417 |
| 2015/0374908 A1 | 12/2015 | Piferi |
| 2016/0074626 A1* | 3/2016 | Weadock ........... A61K 31/4375 600/3 |
| 2016/0100895 A1* | 4/2016 | Piferi ..................... A61B 90/11 606/130 |
| 2016/0213312 A1 | 7/2016 | Singh et al. |
| 2016/0346505 A1 | 12/2016 | Gill et al. |
| 2017/0197017 A1 | 7/2017 | Martin |
| 2017/0232229 A1 | 8/2017 | Flores et al. |
| 2018/0303560 A1 | 10/2018 | Pandey et al. |
| 2019/0255282 A1 | 8/2019 | Inukai et al. |
| 2019/0346516 A1 | 11/2019 | Piferi |

FOREIGN PATENT DOCUMENTS

| | | |
|---|---|---|
| EP | 1 334 740 A1 | 8/2003 |
| EP | 1 482 851 A1 | 12/2004 |
| EP | 1 491 154 A1 | 12/2004 |
| GB | 1 255 551 | 12/1971 |
| JP | 2002-509767 A | 4/2002 |
| JP | 2004-147830 A | 5/2004 |
| WO | WO 99/04849 A1 | 2/1999 |
| WO | WO 99/49909 A2 | 10/1999 |
| WO | WO 02/053205 A2 | 7/2002 |
| WO | WO 03/077785 A1 | 9/2003 |
| WO | WO 2004/031348 A2 | 4/2004 |
| WO | WO 2008/020237 A2 | 2/2008 |
| WO | WO 2008/020241 A2 | 2/2008 |
| WO | WO 2008/144585 A1 | 11/2008 |
| WO | WO 2008/144775 A1 | 11/2008 |
| WO | WO 2009/042135 A2 | 4/2009 |
| WO | WO 2009/047490 A2 | 4/2009 |
| WO | WO 2009/066130 A1 | 5/2009 |
| WO | WO 2009/101397 A1 | 8/2009 |
| WO | WO 2010/040970 A2 | 4/2010 |
| WO | WO 2011/098768 A1 | 8/2011 |
| WO | WO 2011/098769 A1 | 8/2011 |
| WO | WO 2012/178169 A2 | 12/2012 |
| WO | WO 2013/050148 A1 | 4/2013 |
| WO | WO 2014/089373 A1 | 6/2014 |
| WO | 2019030761 A1 | 2/2019 |

OTHER PUBLICATIONS

Bankiewicz et al. "Convection-Enhanced Delivery of AAV Vector in Parkinsonian Monkeys; In Vivo Detection of Gene Expression and Restoration of Dopaminergic Function Using Pro-drug Approach" *Experimental Neurology* 164:2-14 (2000).

Chen et al. "Variables affecting convection-enhanced delivery to the striatum: a systematic examination of rate of infusion, cannula size, infusate concentration, and tissue-cannula sealing time" *Journal of Neurosurgery* 90:315-320 (1999).

Chen et al. "Combination Therapy with Irinotecan and Protein Kinase C Inhibitors in Malignant Glioma" *Cancer* 97(9 Suppl):2363-2373 (2003).

Chen et al. "Surface properties, more than size, limiting convective distribution of virus-sized particles and viruses in the central nervous system" *Journal of Neurosurgery* 103:311-319 (2005).

Cunningham et al. "Distribution of AAV-TK following intracranial convection-enhanced delivery into rats" *Cell Transplantation* 9(5):585-594 (2000) (Abstract Only).

Groothuis, Dennis R. "The blood-brain and blood-tumor barriers: A review of strategies for increasing drug delivery" *Neuro-Oncology* 2:45-59 (2000).

Hadaczek et al. "Convection-Enhanced Delivery of Adeno-Associated Virus Type 2 (AAV2) into the Striatum and Transport of AAV2 Within Monkey Brain" *Human Gene Therapy* 17:291-302 (2006).

Hadaczek et al. "The 'Perivascular Pump' Driven by Arterial Pulsation is a Powerful Mechanism for the Distribution of Therapeutic molecules within the Brain" *Molecular Therapy* 14(1):69-78 (2006).

Krauze et al. "Reflux-free cannula for convection-enhanced high-speed delivery of therapeutic agents" *Journal of Neurosurgery* 103:923-929 (2005).

Krauze et al. "Real-time Imaging and Quantification of Brain Delivery of Liposomes" *Pharmaceutical Research* 23(11):2493-2504 (2006).

Laske et al. "Chronic interstitial infusion of protein to primate brain: determination of drug distribution and clearance with single-photon emission computerized tomography imaging" *Journal of Neurosurgery* 87:586-594 (1997).

Lieberman et al. "Convection-enhanced distribution of large molecules in gray matter during interstitial drug infusion" *Journal of Neurosurgery* 82:1021-1029 (1995).

Lonser et al. "Successful and safe perfusion of the primate brainstem: in vivo magnetic resonance imaging of macromolecular distribution during infusion" *Journal of Neurosurgery* 97:905-913 (2002).

Mamot et al. "Extensive distribution of liposomes in rodent brains and brain tumors following convection-enhanced delivery" *Journal of Neuro-Oncology* 68:1-9 (2004).

Mardor et al. "Monitoring Response to Convection-enhanced Taxol Delivery in Brain Tumor Patients Using Diffusion-weighted Magnetic Resonance Imaging" *Cancer Research* 61:4971-4973 (2001).

Marshall et al. "Biocompatibility of Cardiovascular Gene Delivery Catheters with Adenovirus Vectors: An Important Determinant of the Efficiency of Cardiovascular Gene Transfer" *Molecular Therapy* 1(5):423-429 (2000).

Morrison et al. "High-flow microinfusion: tissue penetration and pharmacodynamics" *American Journal of Physiology—Regulatory, Integrative and Comparative Physiology* 266:R292-R305 (1994).

(56) References Cited

OTHER PUBLICATIONS

Morrison et al. "Focal delivery during direct infusion to brain: role of flow rate, catheter diameter, and tissue mechanics" *American Journal of Physiology—Regulatory, Integrative and Comparative Physiology* 277:R1218-R1229 (1999).
Naimark et al. "Adenovirus-Catheter Compatibility Increases Gene Expression After Delivery to Porcine Myocardium" *Human Gene Therapy* 14:161-166 (2003).
Pardridge, William M. "Drug Delivery to the Brain" *Journal of Cerebral Blood Flow and Metabolism* 17:713-731 (1997).
Pardridge, William M. "The Blood-Brain Barrier: Bottleneck in Brain Drug Development" *NeuroRx: The Journal of the American Society for Experimental NeuroTherapeutics* 2:3-14 (2005).
Patel et al. "Intraputamenal Infusion of Glial Cell Line-Derived Neurotrophic Factor in PD: A Two-Year Outcome Study" *Annals of Neurology* 57:298-302 (2005).
Qureshi et al. "Multicolumn Infusion of Gene Therapy Cells into Human Brain Tumors: Technical Report" *Neurosurgery* 46(3):663-669 (2000) (Abstract Only).
Richardson et al. "Interventional Mri-guided Putaminal Delivery of AAV2-GDNF for a Planned Clinical Trial in Parkinson's Disease" *Molecular Therapy* 19(6):1048-1057 (2011).
Rogawski, Michael A. "Convection-Enhanced Delivery in the Treatment of Epilepsy" *Neurotherapeutics: The Journal of the American Society for Experimental NeuroTherapeutics* 6:344-351 (2009).
Saito et al. "Convection-Enhanced Delivery of Tumor Necrosis Factor-Related Apoptosis-Inducing Ligand with Systemic Administration of Temozolomide Prolongs Survival in an Intracranial Glioblastoma Xenograft Model" *Cancer Research* 64:6858-6862 (2004).
Saito et al. "Distribution of Liposomes into Brain and Rat Brain Tumor Models by Convection-Enhanced Delivery Monitored with Magnetic Resonance Imaging" *Cancer Research* 64:2572-2579 (2004).
Tsui et al. "Stability of Adenoviral Vectors Following Catheter Delivery" *Molecular Therapy* 3(1):122-125 (2001).
Vogelbaum, Michael A. "Convection enhanced delivery for the treatment of malignant gliomas: symposium review" *Journal of Neuro-Oncology* 73:57-69 (2005).
Westphal et al. "Perspectives of cellular and molecular neurosurgery" *Journal of Neuro-Oncology* 70:255-269 (2004).
Hanley et al. "Safety and efficacy of minimally invasive surgery plus recombinant tissue plasminogen activator in intracerebral haemorrhage evacuation (MISTIE): a randomised, phase 2 trial" The Lancet Neurology, 15 (12):1228-1237 (2016).
Mould et al. "Minimally Invasive Surgery plus rt-PA for Intracerebral Hemorrhage Evacuation (MISTIE) Decreases Perihematomal Edema" Stroke, 44(3):627-634 (2013).
Statement on Inventorship Dispute (1 page) (Oct. 5, 2021).

* cited by examiner

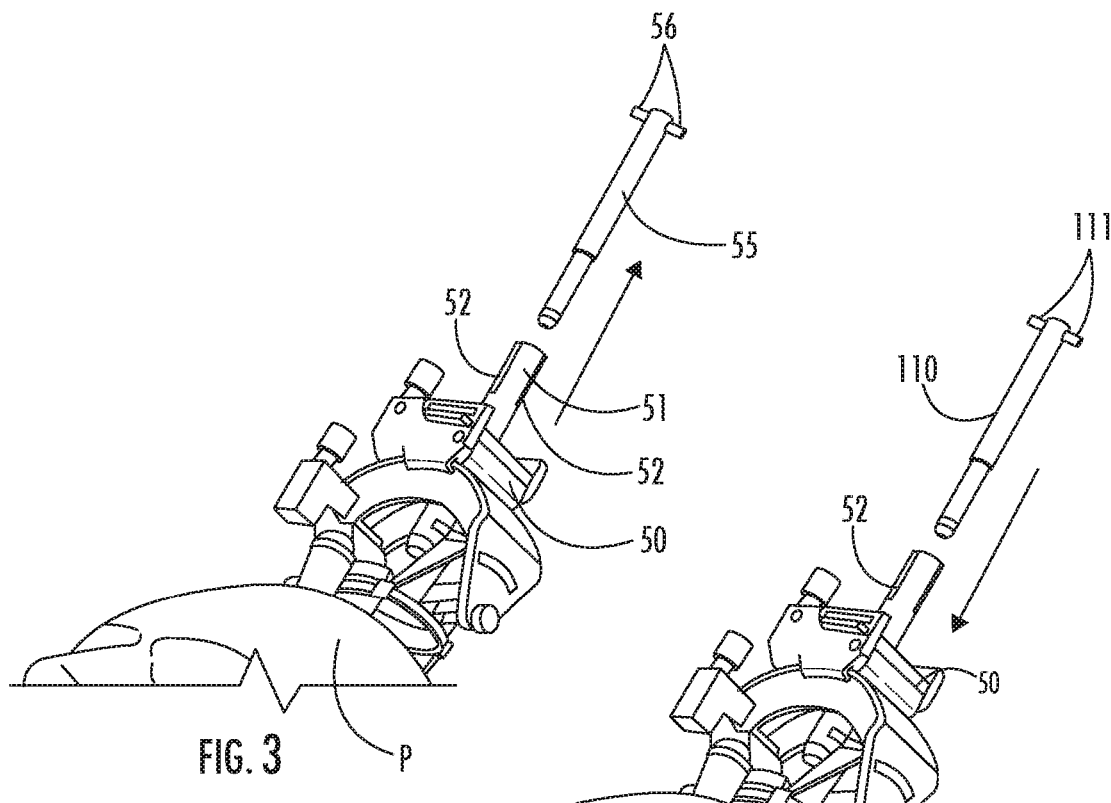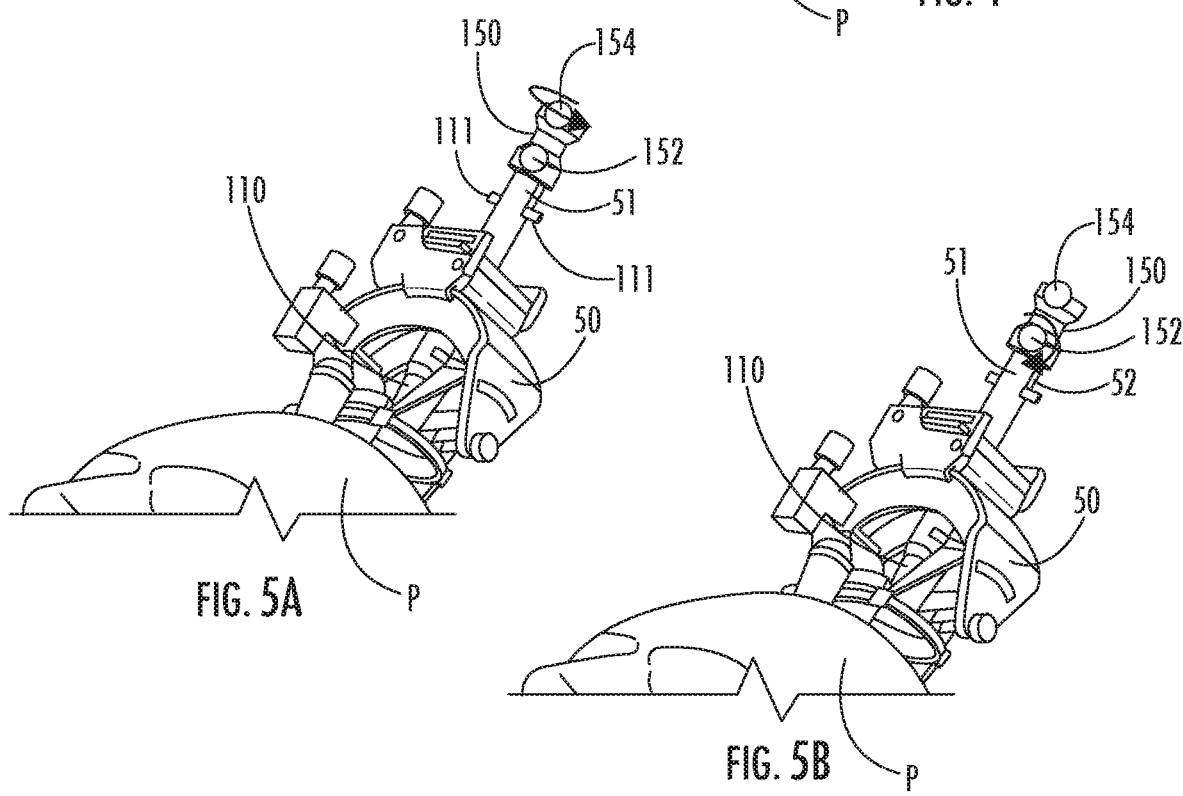

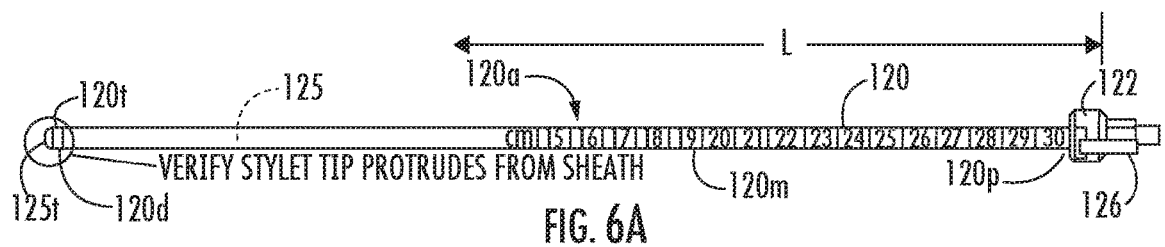
FIG. 6A
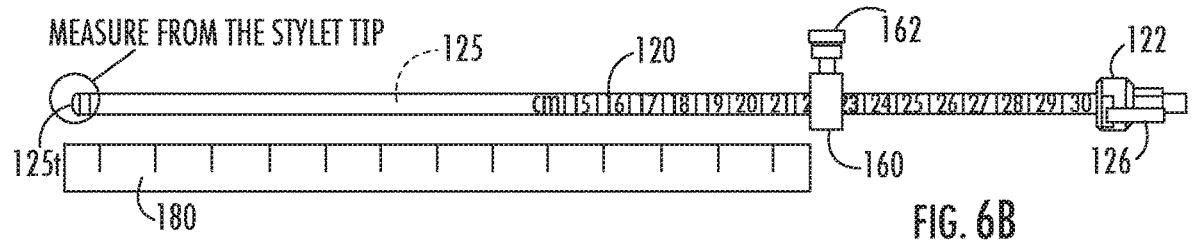
FIG. 6B
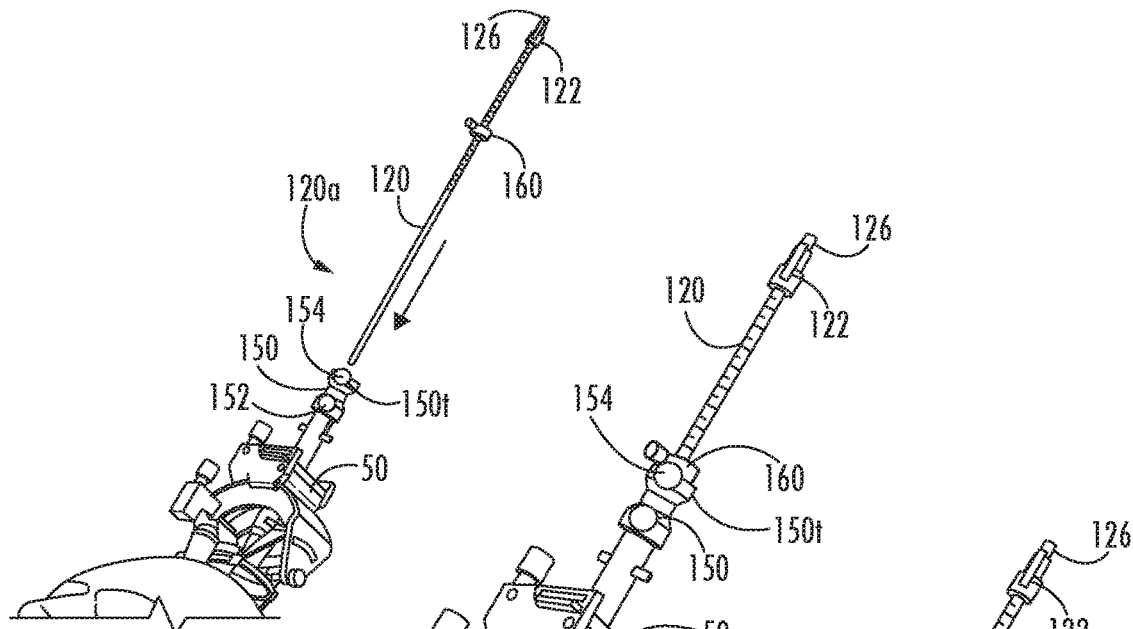
FIG. 7A
FIG. 7B
FIG. 7C

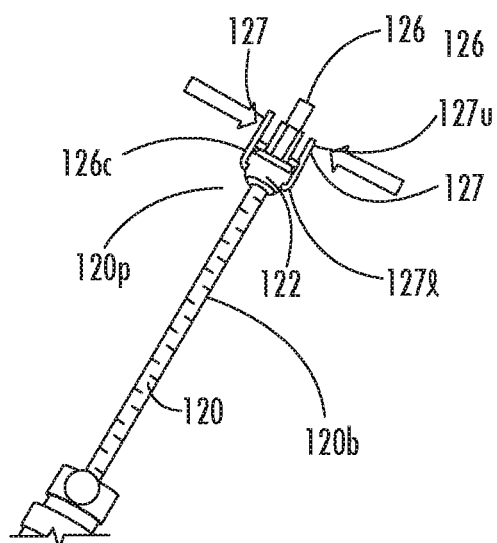
FIG. 8A
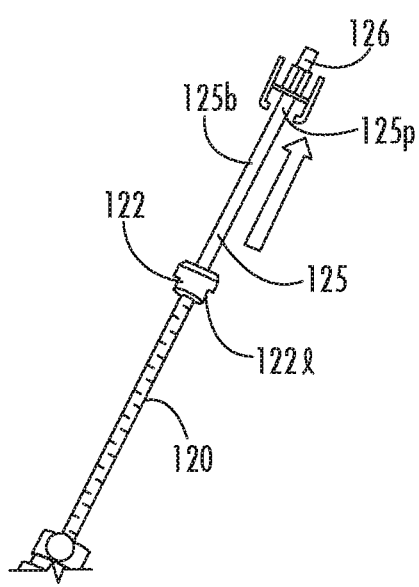
FIG. 8B
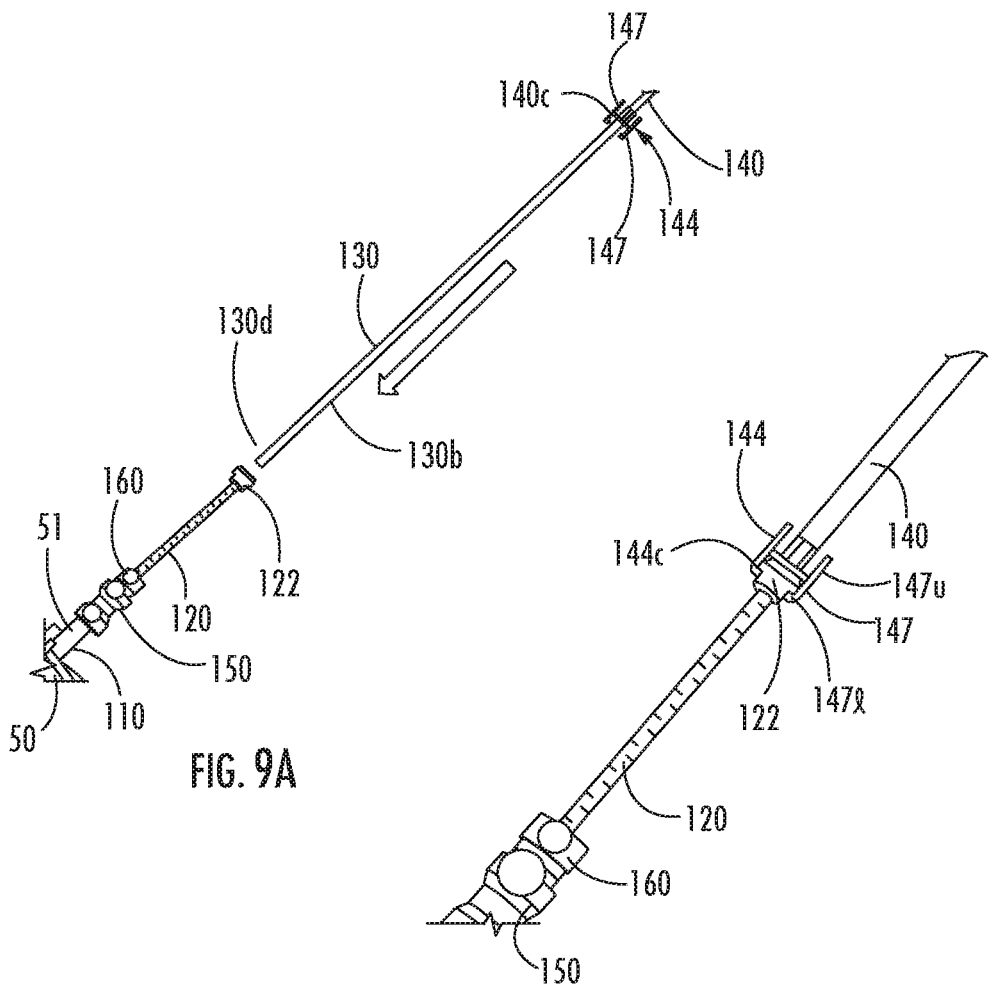
FIG. 9A
FIG. 9B

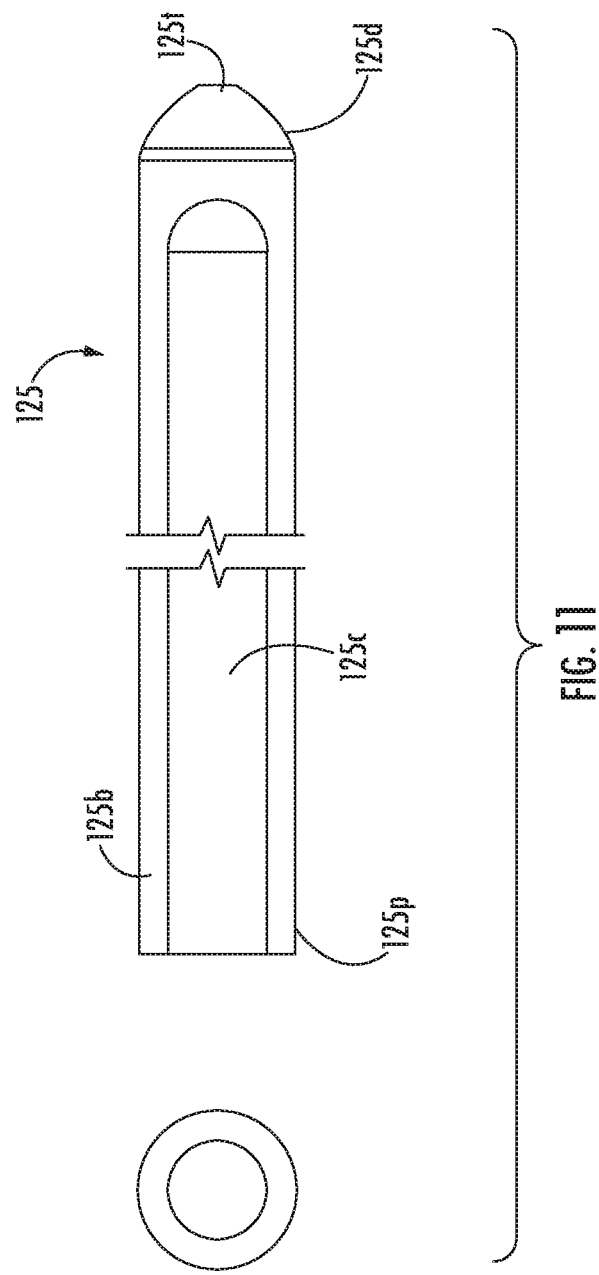

MRI COMPATIBLE INTRABODY FLUID TRANSFER SYSTEMS AND RELATED DEVICES AND METHODS

RELATED APPLICATIONS

This application claims the benefit of and priority to U.S. Provisional Application Ser. No. 62/668,920, filed May 9, 2018, the contents of which are hereby incorporated by reference as if recited in full herein.

FIELD OF THE INVENTION

The present invention relates generally to medical devices and systems and, more particularly, to devices and systems for delivering and/or withdrawing substances in vivo, and may be particularly suitable for MRI-guided aspiration procedures.

BACKGROUND

Various medical procedures require that a substance be aspirated or delivered (e.g., infused) into a prescribed region of a patient, such as to a deep brain target. It may be important or critical that the substance be delivered with high accuracy to the target region in the patient and without undue trauma to the patient.

For example, there are people that have abnormal structures that form in the brain. These structures can be liquid or semi-liquid (soft tissue) in nature. Some examples are fluid-filled cysts, colloid cysts, and large blood clots. When these structures exert pressure on the surrounding areas, various symptoms such as blurry vision, difficulty speaking, or loss of coordination may occur.

Once it is determined that one of these structures is the cause of the problem, physicians determine how to decompress the affected area. In some cases, surgical resection is performed. However, for structures that are deep in the brain and/or extend deep into the brain, surgical resection can be undesirable or not feasible.

One option is to aspirate fluid from the structure to debulk it. Debulking the structure can relieve pressure on the surrounding areas. This can be desirable as it can be performed in a less invasive manner than surgical resection. The current procedure, though, requires that a surgical navigation system be used with pre-op images to position an endoscope trochar, a biopsy needle, or some other aspirating device. Initial position can be important, as the surgeon will target a point in which a single aspiration attempt can withdraw a large percentage of fluid.

Once the surgeon places the device, the intrabrain structure is aspirated. Afterward, the patient is transported to a CT scanner so that the surgeon can determine how much debulking of the structure was accomplished. If the surgeon thinks that further debulking is necessary, the patient is transported back to the surgical room where the navigation procedure is repeated and more fluid is extracted. The patient is then again transported back to the CT scanner, and another CT scan is performed after the subsequent debulking procedure.

The conventional debulking process is costly, time-consuming, and potentially exposes the patient to a higher risk of infection because of the transportation from room to room.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the invention are directed to MRI compatible fluid transfer devices and systems for transferring fluid to or from a subject and may be particularly suitable for aspiration procedures.

Embodiments of the invention are directed to an MRI compatible surgical device that includes a semi-rigid polymeric cannula body coupled to flexible tubing. The cannula body has a longitudinally extending open through channel and is formed of medical grade polyimide tubing with a wall thickness in a range of about 0.005-0.025 inches. The cannula body has a maximal intrabody size in a range of about 10 F-16 F. A distal end of the flexible tubing or a proximal end of the cannula body includes a guide sheath clip connector with longitudinally extending handles. Upper end portions of the handles flex inward to pivot lower end portions outward to disengage a target device.

The wall thickness of the medical grade polyimide tubing can be in a range of about 0.009-0.010 inches.

Other embodiments are directed to an MRI compatible intrabody guide sheath that includes a semi-rigid polymeric guide sheath body. The guide sheath has an axially extending open through channel with opposing proximal and distal ends. In position, the distal end of the guide sheath extends a distance into a subject while the proximal end is external to the subject. The guide sheath body is formed of extruded medical grade PEEK and has a maximal outer diameter of between 12 Fr and 19 Fr. The guide sheath body has a radially outwardly extending external hub adjacent the proximal end. The distal end is tapered and the guide sheath body has a length in a range of 10-16 inches, a wall thickness of about 0.020 inches, and an inner diameter in a range of 0.168 inches and 0.220 inches.

The guide sheath can include measurement indicia on an external wall thereof.

The guide measurement indicia can include or be a graduated scale of distance extending over a sub-length of the guide sheath body with a segment adjacent the distal end being devoid of the graduated scale.

The measurement indicia can include a graduated scale that starts at a distance value that is greater than 10 cm at a location spaced apart from the distal end in a range of 1-8 cm and extends to the proximal end.

The guide sheath can be in combination with a stylet releasably coupled to the guide sheath body. The stylet can have a guide sheath connector on a proximal end portion thereof, wherein the guide sheath connector is a clip with longitudinally extending handles that extend a distance above the hub, and wherein upper end portions of the handles flex inward to pivot lower end portions outward to disengage the hub.

Yet other embodiments are directed to surgical fluid transfer systems that include a device guide comprising an axially extending open through channel and a semi-rigid guide sheath. The guide sheath is configured to slidably extend through the open through channel of the device guide and has an axially extending open through channel with opposing proximal and distal ends. The guide sheath has a length that is longer than a length of the device guide. The guide sheath includes a radially outwardly extending hub adjacent the proximal end. In position, the distal end of the guide sheath extends a distance into a subject while the proximal end is external to the subject. The systems also include a stylet releasably coupled to the guide sheath. When fully assembled to the guide sheath, the stylet extends through the open through channel of the guide sheath and has a distal end that extends a distance out of a distal end of the guide sheath. The stylet has an extruded polymeric body with a hollow core and a solid tapered tip. The stylet has a proximal end portion with a connector that releasably attaches to the hub. The systems further include a cannula coupled to flexible tubing and comprising longitudinally opposing proximal and distal ends. The flexible tubing has a distal end that is sealably coupled to the proximal end of the cannula. In use, the flexible tubing and the proximal end of the cannula reside external to the subject. The cannula is releasably interchangeably coupled to the guide sheath, and, in position, the cannula extends through the guide sheath and has a distal end that extends a distance out of the distal end of the guide sheath.

The guide sheath can include measurement indicia on an external wall thereof.

The connector can be a clip with longitudinally extending handles that extend a distance above the hub. Upper end portions thereof can flex inward to pivot lower end portions outward to disengage the hub.

The distance that the stylet and the cannula extend out of the distal end of the guide sheath can be the same, optionally in a range of about 3-5 mm.

The flexible tubing can have a luer lock connector on a proximal end thereof and a guide sheath connector on the distal end thereof.

The flexible tubing can have a guide sheath connector on a proximal end portion thereof that releasably attaches to the hub.

The guide sheath connector can be a clip with longitudinally extending handles that extend a distance above the hub. Upper end portions thereof can flex inward to pivot lower end portions outward to disengage the hub.

The system can further include an adapter with a longitudinally extending through channel. The adapter can have upper and lower spaced apart lock members. The guide sheath can be configured to extend through the adapter and the upper lock member can be configured to lock against the guide sheath.

The system can include a depth stop that slidably couples to the guide sheath and is adjustable along a length of the guide sheath. The depth stop can abut a top surface of the adapter to hold the guide sheath in a fixed position.

The system can further include a trajectory guide adapted to mount to a subject. The trajectory guide can have a tubular support member with an open through channel that holds the device guide and receives a bottom portion of the adapter.

The device guide, the guide sheath, the stylet and the cannula with the flexible tubing can all MRI compatible polymeric devices that can be provided in a kit for an aspiration procedure.

Yet other embodiment are directed to an aspiration system that includes: a trajectory guide; a device guide held by the trajectory guide; an adapter with a longitudinally extending through channel and upper and lower lock members; a semi-rigid polymeric guide sheath with opposing proximal and distal ends and a longitudinally extending open through channel. The guide sheath further includes an outer wall with an outwardly extending hub adjacent the proximal end. The guide sheath extends through the device guide and adapter. The upper lock member of the adapter is lockable against the guide sheath. The systems also include a stylet with a guide sheath connector on a proximal end portion thereof releasably attachable to the guide sheath. The stylet has a polymeric body with a closed tapered tip that extends a distance out of the distal end of the guide sheath. The system further includes a semi-rigid polymeric cannula coupled to flexible tubing. A distal end of the flexible tubing or a proximal end of the cannula comprises a guide sheath connector that is also, interchangeably, releasably attachable to the guide sheath in place of the stylet. When coupled to the guide sheath, a distal end of the cannula extends a distance out of the distal end of the guide sheath.

The distal end of the cannula and the tip of the stylet can extend out of the distal end of the guide sheath a fixed common distance in a range of about 3-5 mm.

The system can also include a syringe coupled to a proximal end of the flexible tubing to thereby allow a user to aspirate fluid from the subject through the cannula and flexible tubing.

The stylet can have an extruded polymeric body with a hollow core and a solid tapered tip.

The cannula can have a body of medical grade polyimide tubing with a wall thickness in a range of about 0.005-0.025 inches, optionally in a range of about 0.009-0.010 inches. The cannula can have a maximal intrabody size of about 10 Fr-16 Fr, such as one of 10 Fr, 12 Fr, 14 Fr or 16 Fr.

The system can further include a depth stop on the guide sheath residing below the hub.

The outer wall of the guide sheath can include external measurement indicia.

Yet other embodiments are directed to methods of removing fluid from a target intrabody site, during an MRI guided surgical procedure. The methods can include: (a) providing a set of MRI compatible components comprising a device guide, a semi-rigid guide sheath (optionally with measurement indicia) configured to slidably extend through the device guide, a stylet releasable coupled to the guide sheath and extending a fixed distance out of a distal end thereto, and a cannula coupled to flexible tubing; attaching the device guide to a trajectory guide mounted to a subject, the trajectory guide defining an entry trajectory axis into the subject to a target site; (b) placing a depth stop at a desired location on the guide sheath, the desired location associated with measurement indicia calculated to place a distal end of the stylet and a distal end of the cannula at the target site when the guide sheath is attached to the trajectory guide; (c) inserting the guide sheath and stylet, coupled together as an assembly, through the open channel of the device guide; (d) removing the stylet from the guide sheath; then (e) inserting the cannula into the guide sheath so that a distal end thereof resides at the target site; and (f) removing fluid from the target site through the cannula and flexible tubing while the subject is in a magnet of an MR Scanner during the MRI guided surgical procedure.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 3 is a side perspective view of a trajectory guide coupled to a subject that can serially interchangeably hold a targeting cannula and one or more of the components shown in FIG. 2 according to embodiments of the present invention.

FIG. 4 is a side perspective view of the trajectory guide shown in FIG. 3 that slidably couples to the device guide of the devices shown in FIG. 2 according to embodiments of the present invention.

FIGS. 5A and 5B are side perspective views of the trajectory guide holding the device shown in FIG. 4 and also coupled to the adapter shown in FIG. 2 according to embodiments of the present invention.

FIG. 6A is an enlarged view of the guide sheath shown in FIG. 2.

FIG. 6B is an enlarged view of the guide sheath shown in FIG. 6A coupled to a depth stop according to embodiments of the present invention.

FIGS. 7A-7C are side perspective views of an exemplary sequence of actions for attaching the guide sheath and stylet to the trajectory guide shown in FIG. 3 according to embodiments of the present invention.

FIGS. 8A and 8B are enlarged partial views of the guide sheath and stylet shown in FIGS. 7A-7C illustrating an exemplary detachment sequence of the stylet while the guide sheath remains in position coupled to the trajectory guide according to embodiments of the present invention.

FIGS. 9A and 9B are enlarged side perspective views of an exemplary attachment sequence for attaching the guide cannula to the guide sheath held by the trajectory guide according to embodiments of the present invention.

FIG. 11 is a section view of an example stylet body according to embodiments of the present invention.

DETAILED DESCRIPTION

Figure 1:
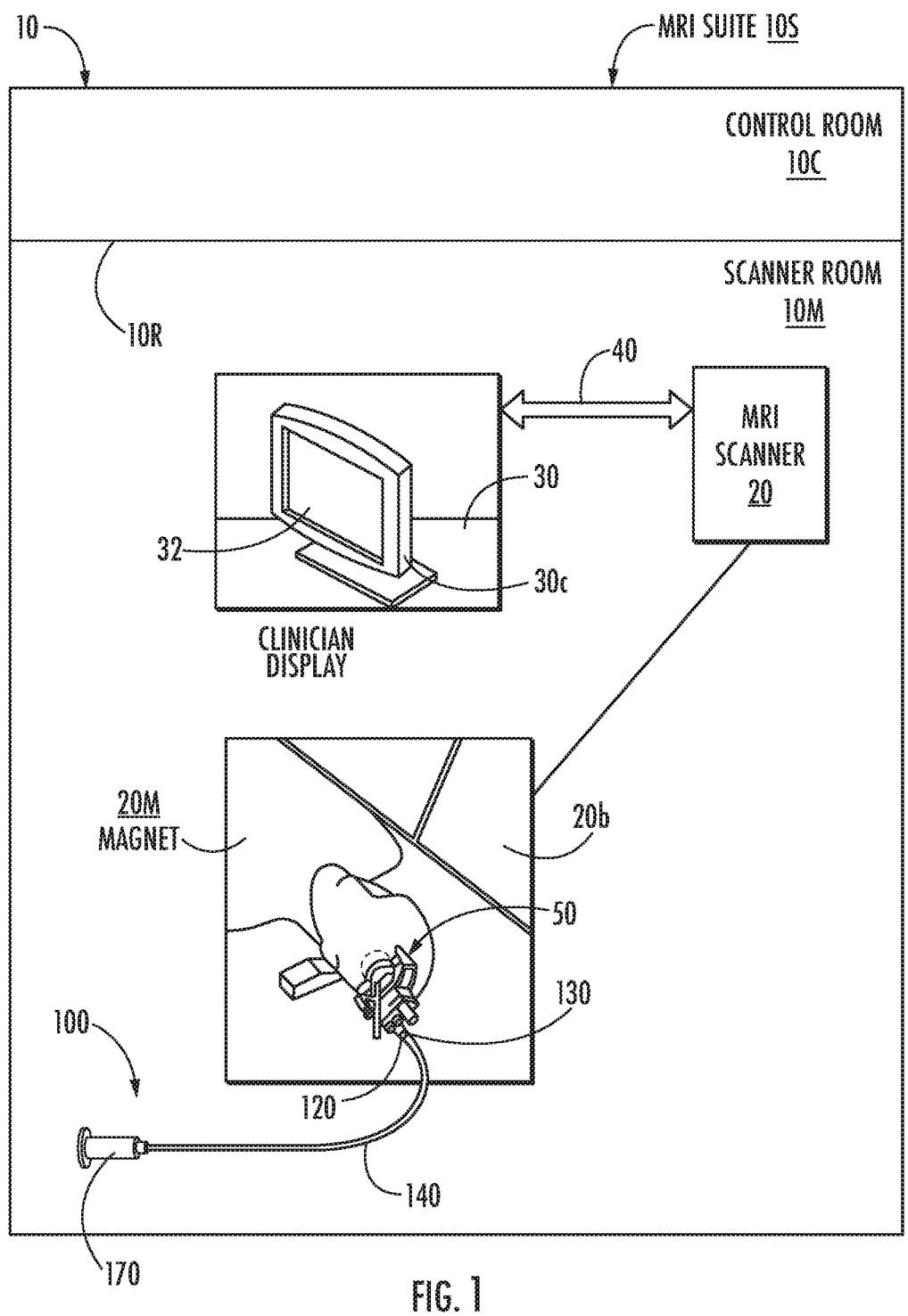
FIG. 1 is a schematic illustration of an MRI-guided interventional system in which embodiments of the present invention may be utilized.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The abbreviations "FIG." and "Fig." are used interchangeably with the word "Figure" to refer to the drawings.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

The term "about," as used herein with respect to a value or number, means that the value or number can vary by +/−twenty percent (20%).

The term "monolithic" means that the component (e.g., needle) is formed of a single uniform material.

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T, such as 2.0 T and 3.0 T, for example.

The term "near real time" refers to both low latency and high frame rate. Latency is generally measured as the time from when an event occurs to display of the event (total processing time). For near "real-time" imaging, the frame rate is typically between about 1 fps to about 20 fps, and in some embodiments, between about 3 fps to about 7 fps. The low latency required to be considered "near real time" is generally less than or equal to about 1 second. With respect to imaging, visualizations using near real time MR image data can be presented with a low latency, typically within between about 0.01 ms to less than about 1 second, and with a frame rate that is typically between about 1-20 fps. The MRI-guided interventional system can use the image signal data to dynamically present anatomy and one or more intrabody devices in the visualization in near real-time.

The term "sterile," as used herein, means that a device, kit, and/or packaging meets or exceeds medical/surgical cleanliness guidelines, and typically is free from live bacteria or other microorganisms.

The term "semi-rigid" refers to devices that have sufficient rigidity to have a self-supporting fixed shape (typically straight linear cylindrical shapes) in the absence of applied bending forces but have sufficient flexibility to be able to bend or deflect without breaking in response to forces applied during insertion into or removal from a trajectory guide, then return to its original self-supporting shape upon removal of the applied force(s).

The subject can be any subject, and may be particularly suitable for animal and/or human subjects for e.g., animal studies and/or veterinarian or human treatments.

Some embodiments aspirate fluid from a target intrabody region such as, for example, a brain.

Embodiments of the invention can deliver therapies to the spine.

Embodiments of the invention can deliver therapies to treat or stimulate a desired region of the sympathetic nerve chain. Other uses, inside or outside the brain, nervous system or spinal cord, include stem cell placement, gene therapy or drug delivery for treating physiological conditions, chemotherapy, drugs including replicating therapy drugs. Some embodiments can be used to treat a patient with one or more tumors.

The term "fluid" with respect to fluid being withdrawn from a subject refers to soft tissue, foreign matter, biological matter including cellular material and liquid in a subject.

The term "substance," as used herein, refers to a gas or liquid for delivery to a subject for treating or facilitating diagnosis of a condition and can include bions, stem cells or other target cells to site-specific regions in the body, such as neurological, nerves or other target sites and the like. In some embodiments, stem cells and/or other rebuilding cells or immune therapy products can be delivered into spine, brain or cardiac tissue. Embodiments of the invention can be used to transfer fluid to or from a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Embodiments of the present invention will now be described in further detail below with reference to the figures. FIG. 1 illustrates an MRI-guided interventional system 10 with an MRI scanner 20, a clinician workstation 30 with at least one image processing circuit 30c, at least one display 32, an MRI compatible trajectory guide 50 and a fluid transfer system 100. Embodiments of the fluid transfer system 100 can be utilized in a bore 20b of a magnet 20M of an MRI scanner 20 of the MRI interventional system 10.

The MRI system 10 can be provided as an MRI suite 10S that can have a control room 10C and a separate magnet room 10M holding the MR Scanner 20 as is well known. However, there is no requirement for a separate control room in some embodiments. Generally stated, MRI suites 10S can have a control room 10C with MRI Scanner operating components such as an RF amplifier and control cabinet and a separate scanner room 10M holding a (high field) magnet 20M in which a patient is placed for an MRI procedure. MRI suites are enclosed in a Faraday shield (e.g., RF shielding) in order to electrically isolate sensitive MRI radio receivers and prevent them from picking up RF signals other than those emitted by the patient under examination. An RF-shielded wall 10R typically separates the two rooms. For a typical MRI scanner room 10M, the RF shielding causes at least 100 dB of signal attenuation of signals in the frequency range of 1 Hz to 150 MHz. Optionally, the MRI suite 10S can be configured with fiber optic cables that are coupled to a user interface that can allow a user to direct certain operational actions using the display 32. The display 30 can reside inside the scanner room 10M. See, e.g., U.S. Pat. No. 9,610,048, the contents of which are hereby incorporated by reference as if recited in full herein.

Figure 2:
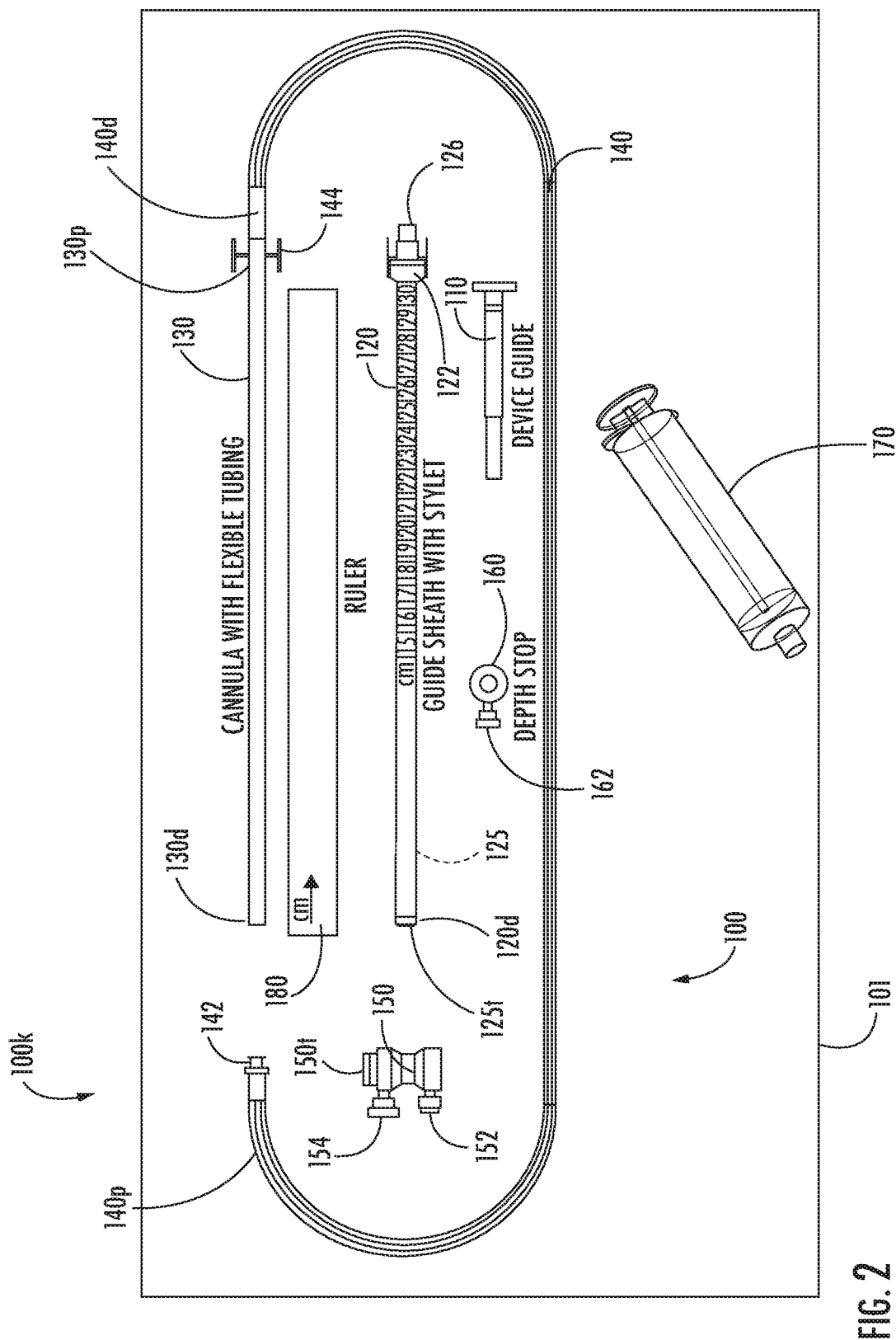
FIG. 2 is a top view of an exemplary set of components for a medical procedure according to embodiments of the present invention.

The fluid transfer system 100 can be provided as components of a kit 100k held in one or more packages 101 as shown in FIG. 2.

The components shown in FIG. 2 can provide an MRI-safe fluid transfer system and when used with a surgical navigation system can allow a surgeon to perform an entire medical procedure in an MRI scanner 20 without requiring transport to another room.

The fluid transfer system 100 can include a device guide 110, a guide sheath 120, a stylet 125 slidably and detachably held by the guide sheath 120, and a cannula 130 coupled to flexible tubing 140. The fluid transfer system 100 can also optionally include at least one syringe 170 which may be provided in the kit 100k or provided separately from the kit 100k.

The flexible tubing 140 can have a proximal end 140p and a distal end 140d. The proximal end 140p can comprise a connector 142 that can attach to the syringe 170. The distal end 140*d* can include a connector 144 that can attach to the guide sheath 120. The flexible tubing 140 with connectors 142, 144 can be provided in the kit 100*k* integrally attached to the cannula 130 as shown. However, the flexible tubing 140 can be provided as a separate component that can be assembled onsite, i.e., for assembly prior to or during a medical procedure. The connector 142 can be a standard (typically female) luer connector.

The kit 100*k* can provide the stylet 125 pre-assembled to the guide sheath 120 as shown. The kit 100*k* can provide the syringe 170 pre-attached to the proximal end of the tubing 140 or the syringe 170, if provided in the kit, can be detached from the tubing 140.

Still referring to FIG. 2, the fluid transfer system 100 can also include an adapter 150, a depth stop 160 and a ruler 180. The ruler 180 can provide graduated scales for positional measurements. The ruler 180 can be a physical ruler that can be removed from the packaging 101 or the ruler 180 can be provided as graduated markings formed or held on a surface of the packaging 101.

All components of the fluid transfer system 100 can be made of MRI compatible materials, typically all made of polymeric materials. The term "MRI compatible materials" means that the materials are non-ferromagnetic and do not magnetically interact with the magnetic field of the magnet. The components used in the MR Scanner room 10S are non-metallic and do not generate heat due to RF coupling during scanning.

The components of the kit 100*k* that are inserted into the body, i.e., brain, during the medical procedure can be configured to be clearly visible as voids (see, 220*v*, FIG. 13) in images 200 generated from an MRI scan, which allows a clinician such as a surgeon to verify that the guide sheath 120, stylet 125 and/or cannula 130 are placed in a desired position in or at a target intrabody region prior to fluid transfer, such as aspiration.

As shown in FIG. 3, a targeting cannula 55 can be inserted into the trajectory guide 50 that is coupled to a subject P for selecting a desired intrabody insertion path. The targeting cannula 55 can be removed (as shown by the arrow) and replaced with the device guide 110 as shown in FIG. 4. The targeting cannula 55 and device guide 110 can both comprise outwardly extending lugs 56, 111 that are slidably received in slots 52 in a tower member 51 of the trajectory guide 50. As shown in FIG. 7A, the guide sheath 120 passes through the device, guide 110 during insertion into the body, i.e., brain. The device guide 110 has an open through channel with a diameter that has a close fit with the outer wall of the guide sheath 120 so that the desired intrabody trajectory can be maintained. The trajectory guide 50 typically provides both X-Y adjustment and pitch and roll adjustment in order to accurately position the targeting cannula 55 and guide sheath 120 at a desired location within a patient. However, the trajectory guide 50 can have other configurations and, in some embodiments, can provide only pitch and roll adjustment without X-Y adjustment. For additional discussion of examples of suitable trajectory guides, see U.S. Pat. No. 8,374,677, and co-pending U.S. patent application Ser. No. 15/934,165, the contents of which are hereby incorporated by reference as if recited in full herein. However, it is noted that other trajectory guide configurations may be used and embodiments of the invention are not limited by the examples of the trajectory guides herein.

Referring to FIGS. 2, 5A and 5B, the adapter 150 can be attached to the trajectory guide 50, in place of a removable cap. The adapter 150 has a sufficiently large inner diameter passage or channel 150*c* that allows the guide sheath 110 to slidably fit therethrough while locking the guide sheath 110 to the tower member 51 of the trajectory guide 50. As shown in FIGS. 5A and 5B, for example, the adapter 150 has a lock member 154 (shown as a thumb screw lock) that holds devices in position, i.e., the guide sheath 120, on the trajectory guide 50 with the distal end 120*d* at the desired intrabody depth.

Figure 5C:
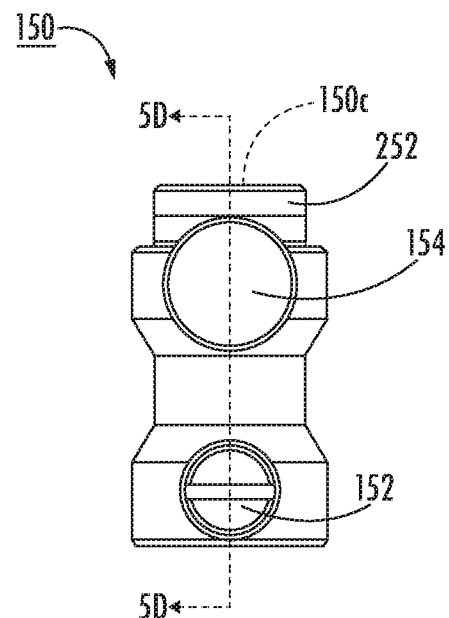
FIG. 5C is an enlarged view of the adapter shown in FIG. 2.
Figure 5D:
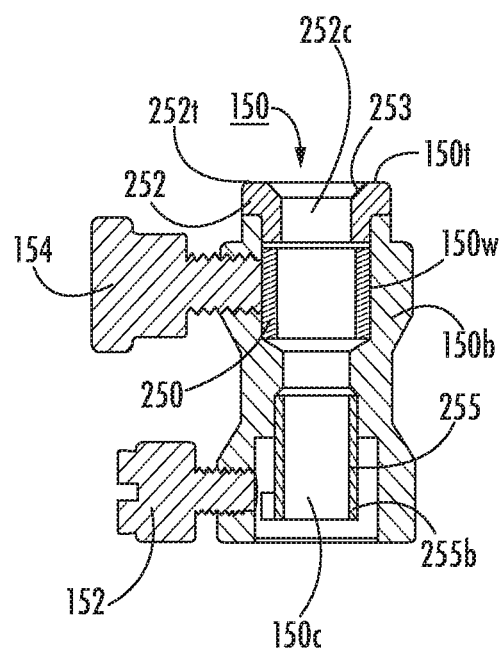
FIG. 5D is a section view taken along line 5D-5D in FIG. 5C, according to embodiments of the present invention.

Referring to FIGS. 5C and 5D, the adapter 150 can have upper and lower lock members 154, 152 and an open longitudinally extending through channel 150*c*. The upper lock member 154 can cooperate with an elastomeric gasket 250 in the channel 150*c*. The gasket 250 squeezes (compresses) against an outer wall of a device held in the channel 150*c*, i.e., the guide sheath 110, without kinking or denting the guide sheath 110 (FIG. 5A). The elastomeric gasket 250 can also increase a grip force with less tightening of the lock member 154 (i.e., thumb screw) relative to the same lock member without such an elastomeric gasket. In some embodiments, a ¼ rotation of the lock member 154 (i.e., thumb screw) can provide about a 1-3 lb tightening/force, i.e., about a 2.7 lb tightening/force, reducing the amount of turns required for sufficient locking/gripping.

Referring to FIG. 5D, the adapter 150 can include a cap 252 with a cylindrical segment that resides in the open channel 150*c*. The cap 252 can have an open channel 252*c* aligned with the open channel of the adapter 150*c*. The cap 252 can hold the gasket 250 in place, aligned with the upper lock member 154. The inner wall 252*w* can taper inward from a first diameter at the top of the cap 252*t* to a smaller diameter providing a chamfer 253 for piloting alignment of devices during insertion. The inner wall 150*w* of the adapter body 150*b* providing the open channel 150*c* can have an enlarged diameter in the segment holding the gasket 250 relative to the diameter of the open channel 150*c* below the gasket 250.

The adapter 150 can also include a locking tab 255 with a bottom 255*b* that engages a circumferentially extending slot 52 in the trajectory guide 50 (tower member 51) allowing for a "twist-lock" to affix the adapter 150 to the trajectory guide 50 and the lower lock member 152 can be tightened to secure the adapter 150 to the tower member 51. The adapter 150 can have a body 150*b* with an inner wall 150*w* that can be sized and configured to provide a suitably sized diameter of the open channel 150*c* that slidably receives the tower member 51.

Referring to FIG. 2 and FIGS. 6A and 6B, the stylet 125 can have a tip 125*t* that is tapered to facilitate atraumatic insertion into the subject. The taper can be over a tip length in a range of about 0.06 inches to 0.11 inches. The stylet 125 can be hollow or solid, typically with a closed forward or tip end 125*t*. When in the fully assembled and operational position inside the guide sheath 120 shown, the stylet 125 can be configured to exit the distal end of the guide sheath 120*d* a fixed distance that is in a range of about 1 mm to about 5 mm. FIG. 11 shows that the stylet 125 can have a primary extruded polymeric body 125*b* with a hollow core 125*c* and a closed tip 125*t*. The stylet 125 can have a length that is in a range of 9-13 inches, such as about 12 inches. The extruded body 125*b* can be semi-rigid with increased flexibility relative to the cannula 130 and guide sheath 120 and can be formed of PEBAX with an outer diameter that is in a range of about 0.160 inches and 0.212 inches and a wall thickness of about 0.025 inches.

The guide sheath 120 can be inserted into the subject (i.e., brain) to target. It is semi-rigid. It encases or contains the stylet 125 with the stylet tip 125 extending external to the distal end 120*d* of the guide sheath 120. The stylet 125 can be flexible and can be locked into position in the sheath 120 but can be removed once the surgeon verifies that the sheath 120 and stylet 125 are in the desired position in the target. The guide sheath 120 can provide a safe working channel in the subject, i.e., brain, allowing the surgeon to insert and remove the cannula 130 as many times as needed without disturbing tissue more than once with the initial placement of the guide sheath 120. Since the stylet 125 locks on to the guide sheath 120, it can maintain its relative position to the guide sheath 120 even if the guide sheath 120 is retracted or advanced relative to the tower (i.e., tubular) member 51 of the trajectory guide 50.

Referring to FIGS. 2, 9A, 10A, 10B the cannula 130 with flexible tubing 140 can be inserted into the guide sheath 120 as a unit so that fluid transfer, i.e., aspiration may be performed. The cannula 130 and flexible tubing 140 are in fluid communication and form a conduit for transferring fluid, i.e., removing aspirated fluid. The cannula 130 is semi-rigid. It can lock onto the guide sheath 120 in the same manner as the flexible stylet 125. This allows the cannula 130 to maintain its relative position to the guide sheath 120 even if the guide sheath 120 is retracted or advanced. The cannula 130 can have a distal end 130*d* that is flat.

The flexible tubing 140 can have a length that is in a range of 1-4 feet long, more typically in a range of about 2 feet to 3 feet. The flexible tubing 140 is external to the subject P, free of any internal more rigid conduit and, when coupled to the guide sheath 120 while held by the trajectory guide 50 coupled to the subject P, can have a length sufficient to extend out of a bore 20*b* of a magnet 20 when the subject is in the magnet, typically with a head of the subject residing proximate one end of the magnet bore 20*b* (FIG. 12A) but is sufficiently short not to be able to drape to the floor of the scanner room when the patient/subject is on a gantry or bed of the MR Scanner 20. For example, for a brain aspiration procedure, the trajectory guide 50 can be mounted to the skull of the subject P and the tubing 140 can extend a distance of between 1-4 feet, allowing a clinician easy access to operate the syringe 170.

An example workflow for an aspiration procedure carried out entirely in an MRI Suite 10 is summarized below.

Figure 13:
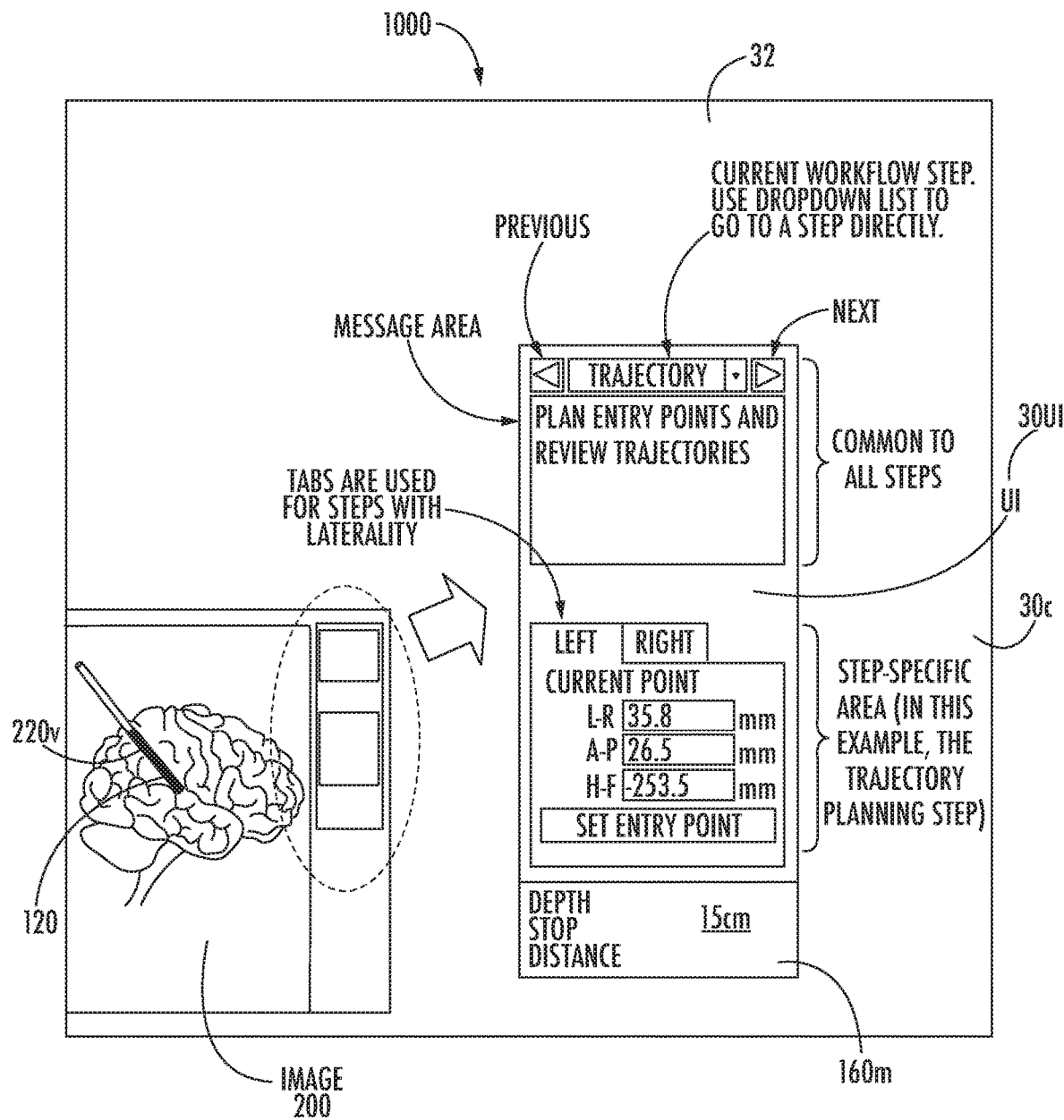
FIG. 13 is a schematic illustration of an example screen display of a surgical navigation system shown on a display according to embodiments of the present invention.

Once the trajectory guide 50 is aligned to a desired trajectory, the targeting cannula 55 can be removed (See FIG. 3). The device guide 110 is then inserted into the trajectory guide 50 and locked it into a bottom circumferentially extending slot 52 by twisting it (See FIG. 4). The adapter 150 is attached to the trajectory guide 50 and twisted to engage a (circumferentially extending) slot(s) 52 at the top of the tower member 51 (See FIG. 5A). The lock member 152 (shown as a lower lock member, i.e., a bottom thumbscrew) is turned to secure it to the tower member 51 (See FIG. 5B). The guide sheath 120 and stylet 125, as an assembly can be obtained from the kit 100*k* (FIG. 2). A visual confirmation can be made to confirm that the Stylet tip 125*t* is protruding from the distal end 120*d* of the guide sheath 120 (See FIG. 6A). Review the depth measurement associated with the target as electronically provided by the surgical navigation system 1000 (FIG. 13). The ruler 180 (FIGS. 2, 6B) to measure corresponding distance on the guide sheath 120. The depth distance from the stylet tip 125*t* can be measured (See FIG. 6B). The depth stop 160 can be placed at the measured distance and locked to guide sheath 120 by tightening a lock member 162, which can be a thumb screw (See FIG. 6B).

The guide sheath 120 and stylet 125 as an assembly 120*a* can be inserted into the trajectory guide 50 until the depth stop 160 bottoms out on or against a top surface 150*t* of the adapter 150 (See FIGS. 7A and 7B). The upper lock member 154 (optionally a thumb screw) on the adapter 150 can be tightened to engage the guide sheath 120 and hold the guide sheath 120 in place (See FIG. 7C).

As the components of the fluid delivery system 100 are MRI safe, scans may be performed while the sheath-stylet assembly 120*a* or sheath 120 and cannula 130 are in position and/or being inserted. An MRI scan can be performed to confirm tip position.

Referring to FIGS. 8A and 8B, the stylet 120 can have a connector 126 that allows the stylet to be detached from the sheath 120. The connector 126 can releasably engage a circumferentially extending hub 122 on a proximal end 120*p* of the sheath 120. The connector 126 can comprise a clip 126*c* with longitudinally extending handles (also interchangeably referred to as "legs") 127. The longitudinally extending legs 127 can extend a distance above the hub 122. The hub 122 can have a greater outer diameter than the primary body of the sheath 120*b* and the primary body of the stylet 125*b*. The hub 122 can have a radially outwardly extending ledge 122*l* that couples to lower ends of the legs 127. A user can (gently) press against (depress) an upper end portion 127*u* of the handles 127, forcing the lower end portions 127*l* to pivot outward and release the hub 122. The stylet 125 can be completely pulled out of the guide sheath 120.

Figure 10A:
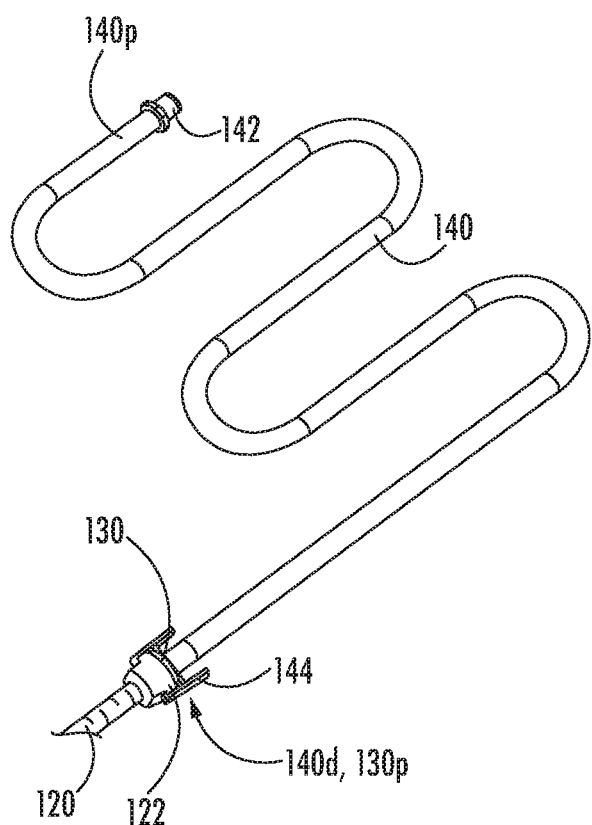
FIGS. 10A and 10B are side perspective views of flexible tubing attached at one end to the guide sheath and attached or attachable to a syringe on the other end according to embodiments of the present invention.

Referring to FIGS. 9A and 9B, the cannula 130 can now be inserted into the guide sheath 120 until a connector 144, which can be a clip 144*c*, bottoms out on the hub 122 of the guide sheath 120. As shown in FIG. 10A, the connector 144 can reside on a distal end of the tubing 140*d* or a proximal end of the cannula 130*p*. The clip 144*c* can lock onto the hub 122. The clip 144*c* can have a common configuration with the stylet clip 126*c*. The clip 144*c* can have longitudinally extending handles (also interchangeably referred to as "legs") 147. The longitudinally extending legs 147 can extend a distance above the hub 122 in the locked position. The hub 122 can have a greater outer diameter than the primary body of the cannula 130*b*. A user can (gently) press against (depress) an upper end portion 147*u* of the handles 147, forcing the lower end portions 147*l* to pivot outward and release the hub 122. The cannula 130 can be completely pulled out of the guide sheath 120.

Figure 10B:
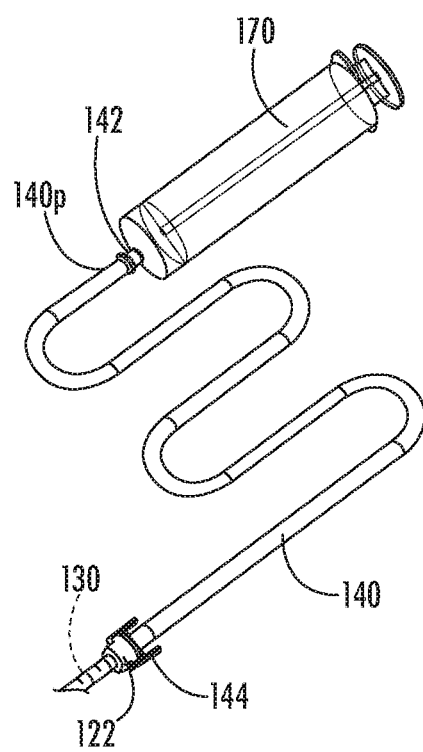

Referring to FIGS. 10A and 10B, the flexible tubing 140 can have a standard (female twist-lock) luer connector 142 at the proximal end 140*p*. A syringe 170 (or other evacuation or pressure source) can be attached to the luer connector 142.

It is noted that although shown for use with a syringe 170, other fluid transfer devices such as pumps for delivery or other vacuum devices such as capillary action devices or tubing and cannisters connected to a wall vacuum source for aspiration may be used.

MR visualization may be used to monitor during a fluid transfer such aspiration with the cannula in position attached to the flexible tubing and with the cannula 130 held by the guide sheath 120 which is coupled to the trajectory guide 50.

To retract the cannula 130, loosen the upper lock member 154 and pull the guide sheath 120 back the desired amount. The upper lock member 154 can then be retightened. The depth stop 160 can be repositioned by loosening the lock member 162 and sliding the depth stop up or down then sliding the guide sheath up or down until the depth stop 160 stops on the top of the adapter 150*t*. The lock member 162 of the depth stop 160 can be retightened. The re-positioning of the cannula 130 and/or depth stop 160 can be repeated as many times as desired.

Embodiments of the invention overcome typical constraints of performing surgical procedures while the patient is in an MR Scanner. The components also have novel designs that promote safety and ease of use. Embodiments of the invention provide a novel combination of materials and sizing to address the MRI issues.

In some embodiments, the guide sheath 120 is semi-rigid. This allows it to maintain appropriate rigidity for accuracy of insertion while also being able to resist being kinked or dented when locked by the lock member 154. However, the configuration also allows it to bend so that the trajectory guide 50 will not experience a high amount of force in the event of a bore collision. Furthermore, to allow for certain targets, the size can be limited to a maximum outer diameter of 0.260" (19 Fr), which is lower than endoscopic trochars used in conventional. The maximal outer diameter may be smaller such as 14 Fr or 16 Fr.

The cannula 130 can be semi-rigid and have MRI compatibility (heat resistant, without magnetic pull, avoiding artifact generation for imaging) and can have sufficient flexibility so it can be slightly bent upon insertion, removal and reinsertion to avoid hitting the inside of the scanner bore. The cannula 130 can be inserted and removed several times from the sheath 120 to flush it out during a surgical procedure, as desired.

The selection of material and wall thickness can be important to maintain these desired properties, particularly given the size constraints. Different combinations of materials and dimensions may yield too rigid a guide sheath (which may make bore collisions unsafe), or too flexible a guide sheath (which compromises accuracy to target). The following tables illustrate example parameters of an example semi-rigid material. To maintain accuracy to a potentially deep target, it is preferred that there is no more than 3.5 mm of deflection at a target 90 mm from the skull surface (Table 1). The 0.15-lb value is an estimate of lateral force applied by brain tissue during insertion of a device. However, in order to deflect in the event of a bore collision, there should be a minimum of 20 mm (2 cm) of deflection with an applied load of 4.0 lb, when the load is applied at 90 mm from where the sheath is supported. The 4.0-lb value is an estimate of the applied force of the bore on the device, as the scanner table is moved from the outside toward the bore center.

TABLE 1

| Maximum Deflection (mm) | Applied Load (lb) | Distance from supported end (mm) |
| --- | --- | --- |
| 2.5 | .15 | 90 |

TABLE 2

| Minimum Deflection (mm) | Applied Load (lb) | Distance from supported end (mm) |
| --- | --- | --- |
| 20 | 4.0 | 90 |

A material with an Elastic Modulus of 1.4-1.6 GPa (typically, about 1.5 GPa) may be particularly suitable for components in a desired dimensional range according to some particular embodiments, as shown in Table 3.

TABLE 3

| OD (in) | ID (in) | Deflection (mm) @ 0.15 lb, 90 mm | Deflection (mm) @ 4.0 lb, 90 mm |
| --- | --- | --- | --- |
| 0.260 | .220 | 1.1 | 29 |
| .233 | .193 | 1.6 | 42 |
| .208 | .188 | 2.3 | 60 |

In some particular embodiments, the guide sheath 120 is made of extruded tubing, such as PEEK tubing, with about a 0.020 inch wall thickness and a length that is in a range of about 8-15 inches, more typically a range of about 9-13 inches.

Referring to FIG. 6A, the guide sheath 120 can have a distal end portion 120d that is tapered over a short distance of about 0.125 inches to have a smaller outer wall dimension at its tip 120t relative to the outer wall dimension spaced apart from the tip 120t. The guide sheath 120 can have graduated scale of measurement markings 120m (interchangeably referred to as "measurement indicia") starting with a value above 0 or 1 (i.e., at 10 cm or greater, shown as starting at 15 cm) residing a distance away from the tip 120d and extending along at least 25% of its length L, optionally in a range of 10 cm to 40 cm to its proximal end portion (FIG. 6A). The markings 120m can start with a measurement of 15 cm at a position that is 2-6 inches from the distal end 120d and increase in measurement values toward the proximal end 120p. The guide sheath 120 can have a different length than the cannula 130. The guide sheath 120 can be shorter than the cannula 130 (and stylet 125) in a range of about 1-3 inches, such as about 1 inch to about 2 inches or 3-5 mm, when fully assembled. The guide sheath 120 can have a maximal size of 19 Fr, such as 12 Fr, 14 Fr or 16 Fr, at least for the intrabody portion. The terms "F" and "Fr" interchangeably refer to the French scale of size of a catheter as is known to those of skill in the art. The guide sheath 120 can have an outer diameter in a range of 0.208 inches and 0.260 inches, an inner diameter in a range of 0.168 and 0.220 inches, and a wall thickness of about 0.020 in some embodiments. The guide sheath 120 can have a length in a range of about 9-13 inches, in some embodiments.

The stylet 125 can be made of 70D durometer PEBA tubing with 0.025" wall thickness that is tipped to create an atraumatic distal end 125t. The stylet 125 is sufficiently flexible so that it can be removed from the guide sheath 120 when the subject P is in the scanner bore, but the wall thickness prevents it from kinking when being bent (which would likely prohibit it from being easily withdrawn out of the sheath 120). This allows the surgeon to remove the stylet to prepare for cannula insertion without having to move the scanner table out of the bore. The stylet 125 can also bend without breaking or kinking in the event of the bore collision of the scanner.

The cannula 130 can have a maximal size of 10 F-16 F, such as about 10 Fr, about 12 Fr, about 14 Fr or about 16 Fr, at least for the intrabody portion. The cannula 130 can be made of (medical grade) polyimide tubing with a wall thickness in a range of about 0.005-0.025 inches, optionally in a range of about 0.009-0.010 inches. Polyimide at this combination of ID and wall thickness is semi-rigid. It provides good rigidity while still being flexible if bent. Again, this is a desirable property, as it allows the surgeon to insert the cannula 130 into the guide sheath 120, even when the trajectory guide's 50 clearance with the scanner bore 20b is small. The wall thickness of the cannula 30 should not be made too thin, as the chance of kinking during bending, thereby obstructing flow, would increase. Also, the wall thickness should be substantial enough so that the wall does not collapse under vacuum pressure during aspiration. In some particular embodiments, the cannula 130 has a small ID of about 0.138 inches and an outer diameter of about 12 Fr, which allows a good cross-sectional area for efficient aspiration of thick or viscous fluid. If the ID is too small, the suction efficiency may be compromised.

The cooperating configurations of the guide sheath 120, the cannula 130, and the stylet 125 promote ease of use and safety. The cannula 130 and stylet 125 can each have a clip-style connector 126c, 144c that allows them to easily lock with and detach from the guide sheath 120. The clips 126c, 144c can be operated single-handedly, and they only require the user to push them over the guide sheath's hub 122 to self-lock. To remove either device from the guide sheath 120, the user need only squeeze the clip's handles 127, 147 and retract the device. This allows the user to insert and remove the cannula 130 and stylet 125 single-handedly while the patient is in the scanner bore.

Also, when the stylet 125 is locked to the guide sheath 120, the stylet tip 125t protrudes a set distance, such as a range of 1-5 mm, more typically a range of 3-5 mm, from the distal end 120d of the sheath 120. When the cannula 130 is locked into the guide sheath 120, it protrudes the same amount as the distal end of the stylet 125t. So, the cannula distal end 130d is always the same position in the target as the stylet distal end 125d was. This allows the surgeon to confirm the position once, exchange the stylet 125 with the cannula 130, and be assured that the cannula tip/distal end 130d is in the same position as the stylet tip 125t. Furthermore, since the stylet 125 and cannula 130 are serially locked to the guide sheath 120, the sheath 120 can be adjusted forward or backward if necessary, and the stylet 125 or cannula 130 travels with it. Therefore, all positional adjustments need only be made to the guide sheath 120.

Most aspiration cannulas are made of metal because the procedure is performed in a completely open surgical environment. Therefore, they can be highly rigid, which is an advantage in maintaining accurate placement. The spatial constraints created by the patient's being in the scanner bore coupled with safety in the MR environment, and maintaining accurate placement of the device, requires a unique combination of rigidity and flexibility. Added to that are the requirements for efficient aspiration, and reduced chance of kinking.

Furthermore, ease of use while the patient is in the scanner bore is achieved by an interchangeable stylet 125 and cannula 130 system which maintains the position of the respective device tips during exchange. The position of the stylet 125 and the cannula 130 can always be maintained relative to the guide sheath 120 when they are locked (fully assembled) together. This allows for easy adjustment of the guide sheath 120 when desired, without needing to confirm the position of the cannula 130 or stylet 125 each time a positional adjustment (advance or retraction) is made.

Figure 12A:
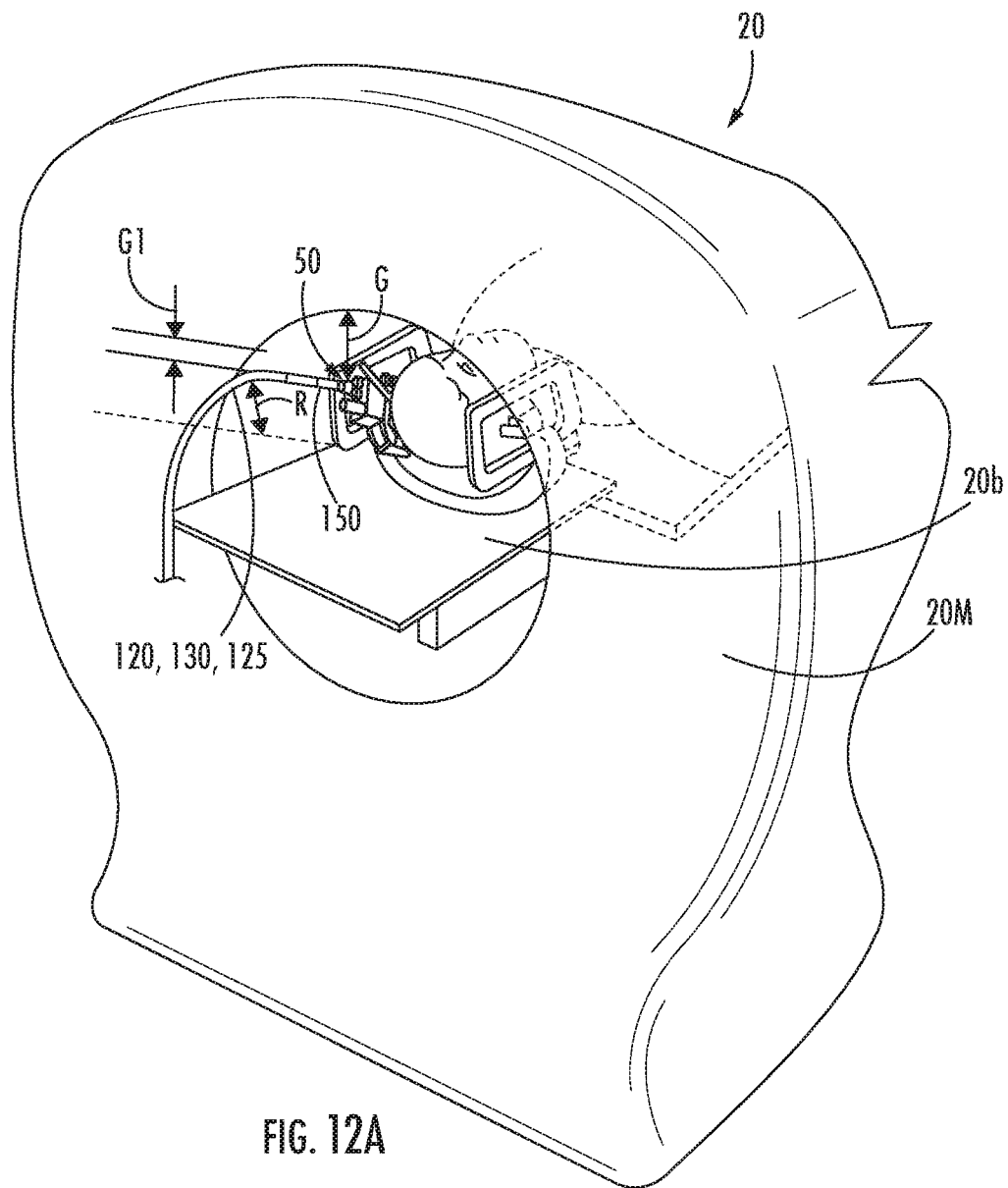
FIG. 12A is an end perspective view of a bore of a magnet with a fluid delivery system in position according to embodiments of the present invention.
Figure 12B:
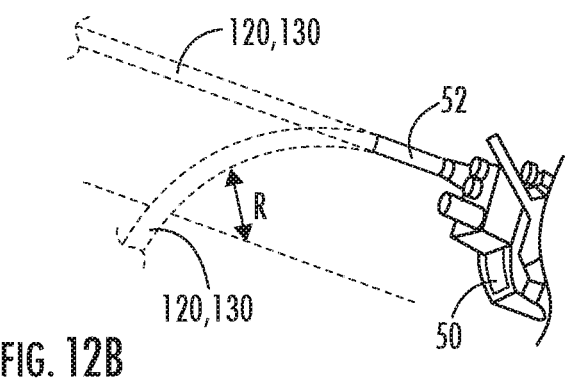
FIG. 12B is a schematic of a portion of the system shown in FIG. 12A illustrating the radius of curvature allowed by the fluid delivery system according to embodiments of the present invention.

FIGS. 12A and 12B illustrate that the stylet 125 and/or cannula 130 can be semi-rigid so as to be able to bend to have a radius of curvature R from its original straight linear shape, such as upon contact with or to avoid a wall of the bore of the magnet 20b when mounted to the trajectory guide 50 or upon removal from the trajectory guide 50. Even if the bore 20b of the magnet does not contact the top of the cannula 130 or stylet 125, the flexibility of both components can allow a surgeon to withdraw/insert them from/into the guide sheath 120 while keeping the patient in the current bore position. The radius of curvature R of the guide sheath 120 can be a maximum of 6.7 cm to allow for curvature of the semi-rigid component to stay within a clearance gap G between a top of the adapter 150 held by the trajectory guide 50 and the wall of the bore that can be a minimum of 7 cm. The radius of curvature R of the cannula 130 and stylet 125 can be a maximum of 5.0 cm to allow for curvature of these components to be withdrawn/inserted with a clearance gap G1 (between the top of the guide sheath 120 and the scanner bore 20b) that can be a minimum of 5.5 cm. This allows the guide sheath 120 to be very close to the scanner bore 20b, while still allowing removal/insertion of the stylet 125 and cannula 130. As shown in FIGS. 12A and 12B, the radius of curvature R can be measured from a non-bent linear line that is parallel to the tower 52 of the trajectory guide 50.

FIG. 13 illustrates a display window of a display 32 from a surgical navigation system 1000 and having a user interface 30UI. The image processing circuit 30c can calculate, and direct the display 32 to provide, a depth stop measurement output 160m (depth stop distance) for a user to set the depth stop 160 on the guide sheath 120. The measurement provided can define a placement of the depth stop 160 at a distance from the stylet tip 125t (FIG. 6A) to the desired location on the guide sheath 120 rather than measured from the distal end of the guide sheath 120d, in some embodiments.

In other embodiments, the measurement direction provided by the display/image processing circuit 30c can allow the user to measure from the distal end of the guide sheath 130 rather than where the stylet tip resides as the cannula distal end extends out of the distal end of the cannula a fixed known distance (i.e., the calculation of the depth stop position on the guide sheath 130 is adjusted for this configuration, as the actual target site reached will be based on the extension distance). The display 32 can also display images, i.e., MRI images 200 with the guide sheath 120, cannula 130 and/or stylet 125 shown as voids 220v in the image(s).

Figure 14:
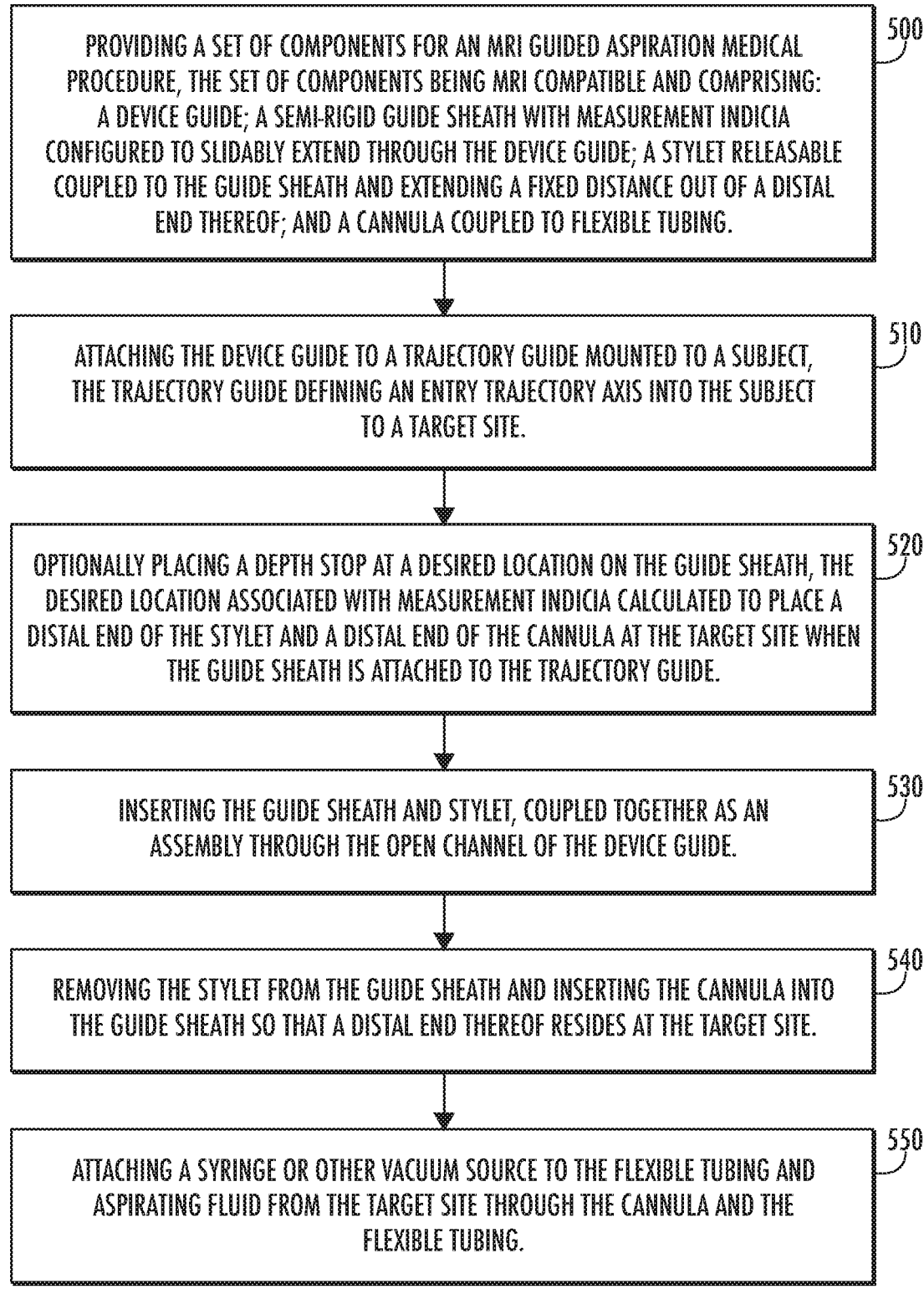
FIG. 14 is a flow chart of example actions that can be carried out according to embodiments of the present invention.

FIG. 14 illustrates an exemplary set of actions that can be used to carry out an MRI-guided medical aspiration procedure. As shown, a set of components for an MRI guided aspiration medical procedure is provided. The set of components being MRI compatible and comprising: a device guide; a semi-rigid guide sheath with measurement indicia configured to slidably extend through the device guide; a stylet releasable coupled to the guide sheath and extending a fixed distance out of a distal end thereof; and a cannula coupled to flexible tubing (block 500).

The device guide is attached to a trajectory guide mounted to a subject, the trajectory guide defining an entry trajectory axis into the subject to a target site (block 510).

A depth stop is placed at a desired location on the guide sheath, the desired location associated with measurement indicia calculated to place a distal end of the stylet and a distal end of the cannula at the target site when the guide sheath is attached to the trajectory guide (block 520).

The guide sheath and stylet, coupled together as an assembly, are inserted through the open channel of the device guide (block 530).

The stylet is removed from the guide sheath and the cannula is then inserted into the guide sheath so that a distal end thereof resides at the target site (block 540).

A syringe or other vacuum source is attached to the flexible tubing and fluid from the target site is aspirated through the cannula and the flexible tubing (block 550).

While the devices have been described herein primarily with reference to MRI-guided insertion and infusion procedures, in some embodiments the devices can be used in procedures without MRI guidance.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A surgical fluid transfer system comprising:
   a device guide comprising an axially extending open through channel;
   a semi-rigid guide sheath, wherein the guide sheath is configured to slidably extend through the open through channel of the device guide, wherein the guide sheath has an axially extending open through channel with opposing proximal and distal ends, wherein the guide sheath has a length that is longer than a length of the device guide, wherein the guide sheath comprises a radially outwardly extending hub adjacent the proximal end, and wherein, in position, a distal end of the guide sheath extends a distance into a subject while the proximal end is external to the subject;
   a stylet releasably coupleable to the guide sheath, wherein, when fully assembled to the guide sheath, the stylet extends through the open through channel of the guide sheath and has a distal end that extends a distance out of the distal end of the guide sheath, wherein the stylet comprises an extruded polymeric body with a hollow core and a solid tapered tip, and wherein the stylet comprises a proximal end portion with a connector that releasably attaches to the hub; and
   a cannula coupled to flexible tubing and comprising longitudinally opposing proximal and distal ends, wherein the cannula is semi-rigid, wherein the flexible tubing has a distal end that is sealably coupled to the proximal end of the cannula, wherein, in use, the flexible tubing and the proximal end of the cannula reside external to the subject, wherein the cannula is releasably interchangeably coupleable to the guide sheath in place of the stylet, and wherein, in position, the cannula extends through the guide sheath and the distal end extends a distance out of the distal end of the guide sheath.

2. The system of claim 1, wherein the guide sheath comprises measurement indicia on an external wall thereof, and wherein the measurement indicia comprises a numerical scale of distance that increases in a direction toward the proximal end of the guide sheath.

3. The system of claim 1, wherein the connector is a clip with longitudinally extending handles each configured to have a straight linear length that extends a distance above the hub and that terminates at lower end portions adjacent a smaller transverse section of the hub, wherein the lower end portions turn inward and face each other across the hub, and wherein upper end portions thereof flex inward to pivot the lower end portions outward to disengage the hub.

4. The system of claim 1, further comprising a depth stop slidably held by the guide sheath that defines a fixed distance as the distance that the distal end of the cannula extends out of the distal end of the guide sheath.

5. The system of claim 4, wherein the distance is in a range of about 3-5 mm.

6. The system of claim 1, wherein the flexible tubing comprises a guide sheath connector on a distal end portion thereof that releasably attaches to the hub.

7. The system of claim 6, wherein the guide sheath connector is a clip with longitudinally extending handles that are parallel to and are spaced outward a distance from an outer surface of the guide sheath and that extend a distance above the hub and terminate at a lower portion of the hub at lower end portions that turn inward toward the hub, and wherein upper end portions thereof flex inward to pivot the lower end portions outward to disengage the hub.

8. The system of claim 1, further comprising an adapter with a longitudinally extending through channel, the adapter comprising a unitary body with upper and lower spaced apart lock members, wherein the upper lock member communicates with an internal gasket that extends a sub-length of the adapter, and wherein the guide sheath is configured to extend through the adapter and only the upper lock member is configured to lock against the guide sheath.

9. The system of claim 8, further comprising a depth stop that slidably couples to the guide sheath and is adjustable along a length of the guide sheath, wherein the depth stop abuts a top surface of the adapter to hold the guide sheath in a fixed position.

10. The system of claim 1, wherein the device guide, the guide sheath, the stylet and the cannula with the flexible tubing are all Mill compatible polymeric devices provided in a kit for an aspiration procedure.

11. The system of claim 1, wherein the cannula is formed of medical grade polyimide tubing with a wall thickness in a range of about 0.005-0.025 inches, and wherein the cannula has a maximal intrabody size in a range of about 10 Fr-16 Fr.

12. The system device of claim 11, wherein the wall thickness of the medical grade polyimide tubing is in a range of about 0.009-0.010 inches.

13. The system of claim 1, wherein the guide sheath is formed of extruded medical grade PEEK and has a maximal outer diameter in a range of 12 Fr and 19 Fr, and wherein the guide sheath has a length in a range of 10-16 inches, a wall thickness of about 0.020 inches, and an inner diameter in a range of 0.168 inches and 0.220 inches.

14. The system of claim 1, wherein the guide sheath comprises a graduated scale of distance extending over a sub-length of a body of the guide sheath with a segment adjacent the distal end being devoid of the graduated scale and with the graduated scale providing units of distance that increase in a direction toward the proximal end of the guide sheath.

15. The system of claim 1, wherein the guide sheath comprises a graduated scale that starts at a distance value that is greater than 10 cm at a location spaced apart from the distal end in a range of 1-8 cm therefrom and extends in increasing order to the proximal end.

16. The system of claim 1, further comprising a guide sheath connector on the distal end of the flexible tubing or the proximal end of the cannula that is configured as a clip with longitudinally extending handles that are parallel to and spaced outward a distance from an outer surface of the cannula and that extend a distance above the hub and that terminate at a lower portion of the hub at lower end portions that turn inward toward the hub, and wherein upper end portions of the handles flex inward to pivot the lower end portions outward to disengage the hub.

17. A surgical fluid transfer system comprising:
a device guide comprising an axially extending open through channel;
a semi-rigid guide sheath, wherein the guide sheath is configured to slidably extend through the open through channel of the device guide, wherein the guide sheath has an axially extending open through channel with opposing proximal and distal ends, wherein the guide sheath has a length that is longer than a length of the device guide, wherein the guide sheath comprises a radially outwardly extending hub adjacent the proximal end, and wherein, in position, a distal end of the guide sheath extends a distance into a subject while the proximal end is external to the subject;
a stylet releasably coupled to the guide sheath, wherein, when fully assembled to the guide sheath, the stylet extends through the open through channel of the guide sheath and has a distal end that extends a distance out of the distal end of the guide sheath, wherein the stylet comprises an extruded polymeric body with a hollow core and a solid tapered tip, and wherein the stylet comprises a proximal end portion with a connector that releasably attaches to the hub;
a cannula coupled to flexible tubing and comprising longitudinally opposing proximal and distal ends, wherein the flexible tubing has a distal end that is sealably coupled to the proximal end of the cannula, wherein, in use, the flexible tubing and the proximal end of the cannula reside external to the subject, wherein the cannula is releasably interchangeably coupled to the guide sheath, and wherein, in position, the cannula extends through the guide sheath and the distal end extends a distance out of the distal end of the guide sheath;
an adapter with a longitudinally extending through channel, the adapter comprising upper and lower spaced apart lock members, wherein the guide sheath is configured to extend through the adapter and the upper lock member is configured to lock against the guide sheath; and
a trajectory guide adapted to mount to the subject, the trajectory guide comprising a tubular support member with an open through channel that holds the device guide and receives a bottom portion of the adapter.

18. An aspiration system, comprising:
a trajectory guide;
a device guide held by the trajectory guide;
an adapter with a longitudinally extending through channel and upper and lower lock members;
a semi-rigid polymeric guide sheath comprising opposing proximal and distal ends and a longitudinally extending open through channel, wherein the guide sheath further comprises an outer wall with an outwardly extending hub adjacent the proximal end, wherein the guide sheath extends through the device guide and adapter, and wherein the upper lock member of the adapter is lockable against the guide sheath;
a stylet with a guide sheath connector on a proximal end portion thereof releasably attachable to the guide sheath, wherein the stylet has a polymeric body with a closed tapered tip that extends a distance out of the distal end of the guide sheath; and
a semi-rigid polymeric cannula coupled to flexible tubing, wherein a distal end of the flexible tubing or a proximal end of the cannula comprises a guide sheath connector that is also, interchangeably, releasably attachable to the guide sheath in place of the stylet, and wherein, when coupled to the guide sheath, a distal end of the cannula extends a distance out of the distal end of the guide sheath.

19. The system of claim 18, wherein the distal end of the cannula and the tip of the stylet extend out of the distal end of the guide sheath a fixed common distance in a range of about 3-5 mm.

20. The system of claim 18, further comprising a syringe coupled to a proximal end of the flexible tubing to thereby allow a user to aspirate fluid from the subject through the cannula and flexible tubing.

21. The system of claim 18, wherein the stylet comprises an extruded polymeric body with a hollow core with an open proximal end and a solid tapered tip defining the closed tapered tip.

22. The system of claim 18, wherein the cannula comprises a body of medical grade polyimide tubing with a wall thickness in a range of about 0.005-0.025 inches, and wherein the cannula has a maximal intrabody size of about 10 Fr-16 Fr.

23. The system of claim 18, further comprising a depth stop on the guide sheath residing below the hub, wherein the upper lock member communicates with an internal gasket that extends a sub-length of the adapter.

24. The system of claim 18, wherein the outer wall of the guide sheath further comprises external measurement indicia comprising a graduated scale thereof provided with units of distance that increase in a direction toward the proximal end of the guide sheath.

25. A method of removing fluid from a target intrabody site, during an MRI guided surgical procedure, comprising:
providing a set of MRI compatible components comprising a device guide, a semi-rigid guide sheath configured to slidably extend through the device guide, a stylet releasably coupled to the guide sheath and extending a fixed distance out of a distal end thereof, and a cannula coupled to flexible tubing;
attaching the device guide to a trajectory guide mounted to a subject, the trajectory guide defining an entry trajectory axis into the subject to a target site;
placing a depth stop at a desired location on the guide sheath, the desired location associated with measurement indicia calculated to place a distal end of the stylet and a distal end of the cannula at the target site when the guide sheath is attached to the trajectory guide, wherein the guide sheath comprises measurement indicia with distance values increasing in a direction toward a proximal end portion of the guide sheath;
inserting the guide sheath and stylet, coupled together as an assembly, through an open channel of the device guide;
removing the stylet from the guide sheath, bending the stylet relative to the device guide during the removal to clear a wall of a bore of a magnet of an MRI scanner; then
inserting the cannula into the guide sheath so that a distal end thereof resides at the target site; and
removing fluid from the target site through the cannula and flexible tubing while the subject is in a magnet of an MR Scanner during the MM guided surgical procedure.

* * * * *

UNITED STATES PATENT AND TRADEMARK OFFICE
CERTIFICATE OF CORRECTION

| | |
|---|---|
| PATENT NO. | : 11,253,237 B2 |
| APPLICATION NO. | : 16/217273 |
| DATED | : February 22, 2022 |
| INVENTOR(S) | : Daly et al. |

It is certified that error appears in the above-identified patent and that said Letters Patent is hereby corrected as shown below:

In the Claims

Column 18, Line 30, Claim 10: Please correct "Mill" to read -- MRI --

Column 20, Line 63, Claim 25: Please correct "MM" to read -- MRI --

Signed and Sealed this
Fifth Day of July, 2022

*Katherine Kelly Vidal*

Katherine Kelly Vidal
*Director of the United States Patent and Trademark Office*